(12) United States Patent  
Wang et al.

(10) Patent No.: US 8,481,459 B2  
(45) Date of Patent: Jul. 9, 2013

(54) CHEMICAL INHIBITORS OF ETHYLENE BIOSYNTHESIS

(75) Inventors: Long-Chi Wang, Taipei (TW); Lee-Chung Lin, Taipei (TW)

(73) Assignee: Academia Sinica, Taipei (TW)

( * ) Notice: Subject to any disclaimer, the term of this patent is extended or adjusted under 35 U.S.C. 154(b) by 219 days.

(21) Appl. No.: 13/160,411

(22) Filed: Jun. 14, 2011

(65) Prior Publication Data

US 2012/0023625 A1    Jan. 26, 2012

Related U.S. Application Data

(60) Provisional application No. 61/354,528, filed on Jun. 14, 2010.

(51) Int. Cl.
*A01N 43/54* (2006.01)
*C07D 239/72* (2006.01)
*C07D 239/70* (2006.01)

(52) U.S. Cl.
USPC ............ 504/240; 544/253; 544/283

(58) Field of Classification Search
USPC .......... 504/189, 240; 544/253, 283
See application file for complete search history.

(56) References Cited

U.S. PATENT DOCUMENTS 6,156,956 A    12/2000 Theologis et al.
2009/0163545 A1*   6/2009 Goldfarb ............... 514/312

OTHER PUBLICATIONS

Barry, Cornelius S., "The Regulation of 1-Aminocyclopropane-1-Carboxylic Acid Synthase Gene Expression during the Transition from System-1 to System-2 Ethylene Synthesis in Tomato," Plant Physiology, vol. 123, pp. 979-986, (Jul. 2000).
Bufler, Gebhard, "Ethylene-Enhanced 1-Aminocyclopropane-1-carboxylic Acid Synthase Activity in Ripening Apples," Plant Phsyiol (1984) 75, 192-195.
Chae et al., "Eto Brute? Role of ACS turnover in regulating ethylene biosynthesis," Trends in Plant Science, vol. 10, No. 6, Jun. 2005.
Christians et al., "The BTB ubiquitin ligases ETO1, EOL1 and EOL2 act collectively to regulate ethylene biosynthesis in *Arabidopsis* by controlling type-2 ACC synthase levels," The Plant Journal (2009) 57, 335-345.
Hansen et al., "Regulation of ACS protein stability by cytokinin and brassinosteroid," Plant J. Feb. 2009, 57(4); 606-614.
Ko et al., "S-Methylmethionine is both a substrate and an inactivator of 1-aminocyclopropane-1-carboxylate synthase," Archives of Biochemistry and Biophysics 421 (2004) 85-90.
Lin et al., "Identification of Novel Inhibitors of 1-Aminocyclopropane-1-carboxylic Acid Synthase by Chemical Screening in *Arabidopsis thaliana*," The Journal of Biological Chemistry, vol. 285, No. 43, pp. 33445-33456, Oct. 22, 2010.
Matarasso et al., "A Novel Plant Cysteine Protease Has a Dual Function as a Regulator of 1-Aminocyclopropane-1-Carboxylic Acid Synthase Gene Expression," The Plant Cell, vol. 17, 1205-1216, Apr. 2005.
Skottke et al., "Protein Phosphatase 2A Controls Ethylene Biosynthesis by Differentially Regulating the Turnover of ACC Synthase Isoforms," PLoS Genetics, Apr. 2011, vol. 7, Issue 4, 1-13.
Tsuchisaka et al., "A Combinatorial Interplay Among the 1-Aminocyclopropane-1-Carboxylate Isoforms Regulates Ethylene Biosynthesis in *Arabidopsis thaliana*," Genetics 183: 979-1003 (Nov. 2009).
Yamagami et al., "Biochemical Diversity Among the 1-Amino-Cyclopropane-1-Carboxylate Synthase Isozymes Encoded by the *Arabidopsis* Gene Family," The Journal of Biological Chemistry, Vo. 278, No. 49, 49102-49112 (Dec. 5, 2003).
Yasuta et al., "New Assay for Rhizobitoxine Based on Inhibition of 1-Aminocyclopropane-1-Carboxylate Synthase," Applied and Environmental Microbiology, Feb. 1999, p. 849-852.
Yoshida et al., "*Arabidopsis* ETO1 specifically interacts with and negatively regulates type 2 1-aminocyclopropane-1-carboxylate synthases," BMC Plant Biology 2005, 5:14, p. 1-13.
Yoshida et al., "The ACC synthase TOE sequence is required for interaction with ETO1 family proteins and destabilization of target proteins," Plant Mol. Biol. (2006) 62:427-437.
Yu et al., "1-Aminocyclopropanecarboxylate Synthase, a Key Enzyme in Ethylene Biosynthesis," Archives of Biochemistry and Biophysis, Vo. 198, No. 1, November, pp. 280-286, 1979.

\* cited by examiner

*Primary Examiner* — Johann R Richter
*Assistant Examiner* — Andriae M Holt
(74) *Attorney, Agent, or Firm* — Wilson, Sonsini, Goodrich & Rosati

(57) ABSTRACT

The present invention provides methods for improving the quality of harvested plants. The present invention also provides novel ACC synthase inhibitors useful for improving the quality of harvested plants.

14 Claims, 8 Drawing Sheets

CHEMICAL INHIBITORS OF ETHYLENE BIOSYNTHESIS

CROSS-REFERENCE

This application claims the benefit of U.S. Provisional Application No. 61/354,528, filed Jun. 14, 2010, which is entirely incorporated herein by reference.

BACKGROUND OF THE INVENTION

Ethylene is an important gaseous phytohormone regulating plant growth and development in processes such as seed germination, root development, leaf and flower senescence, and fruit ripening, and responds to a variety of stresses (Bleecker, et al. (2000) *Annu Rev Cell Dev Biol* 16, 1-18; Johnson, et al. (1998) *Annu Rev Genet* 32, 227-254; Lin, et al. (2009) *J Exp Bot* 60, 3311-3336; Wang, et al. (2002) *Plant Cell* 14 Suppl, S131-151). Because of its versatile functions, ethylene has a critical role in adaptation and survival in plants. In the presence of ethylene, etiolated seedlings display a photomorphogenesis phenotype called the triple response: an exaggerated curvature of the apical hook, radial swelling of the hypocotyl, and shortening of the hypocotyl and root (Ecker, J. R. (1995) *Science* 268, 667-675). The triple response phenotype has been successfully used to identify mutants defective in ethylene biosynthesis or response in *Arabidopsis thaliana* (Ecker, J. R. (1995) *Science* 268, 667-675; Chang, et al. (1993) *Science* 262, 539-544; Guzman, et al. (1990) *Plant Cell* 2, 513-523; Roman, et al. (1995) *Genetics* 139, 1393-1409). Further studies of the ethylene mutants revealed the genetic hierarchy of key components in ethylene biosynthesis and signaling transduction in *Arabidopsis* (Lin, et al. (2009) *J Exp Bot* 60, 3311-3336; Yoo, et al. (2009) *Trends Plant Sci* 14, 270-279). Ethylene signaling is initiated by the interaction between the ethylene ligand and its receptors localized in the endoplasmic reticulum (ER) membrane (Chen, et al. (2002) *J Biol Chem* 277, 19861-19866; Grefen, et al. (2008) *Mol Plant* 1, 308-320). Binding of ethylene to the receptors inactivates a negative regulator, CTR1, which constitutively represses a positive regulator, EIN2 (Bleecker, et al. (1998) *Philos Trans R Soc Lond B Biol Sci* 353, 1405-1412). Ethylene receptors activate CTR1 to suppress EIN2 in the absence of ethylene and therefore, function as negative regulators of the ethylene response (Huang, et al. (2003) *Plant J* 33, 221-233; Qiao, et al. (2009) *Genes Dev* 23, 512-521). It has been proposed that a functional interaction among the ethylene receptors, CTR1, and EIN2 takes place in or near the ER membrane (Chen, et al. (2002) *J Biol Chem* 277, 19861-19866; Bisson, et al. (2009) *Biochem J* 424, 1-6; Gao, et al. (2003) *J Biol Chem* 278, 34725-34732). De-repressed EIN2 stabilizes the otherwise labile transcription factor EIN3 by a yet unknown mechanism (Qiao, et al. (2009) *Genes Dev* 23, 512-521; Alonso, et al. (1999) *Science* 284, 2148-2152; Guo, et al. (2003) *Cell* 115, 667-677; Potuschak, et al. (2003) *Cell* 115, 679-689). As a consequence, EIN3 activates an array of genes responsible for the ethylene response (Chao, et al. (1997) *Cell* 89, 1133-1144; Solano, et al. (1998) *Genes Dev* 12, 3703-3714). Although the ethylene signaling pathway has been elucidated by mainly studying genetic mutants in *Arabidopsis*, additional factors regulating the key components have been revealed by new approaches (Guo, et al. (2003) *Cell* 115, 667-677; Potuschak, et al. (2003) *Cell* 115, 679-689; Yoo, et al. (2008) *Nature* 451, 789-795), which suggests the use of new methodology to study ethylene function.

Ethylene gas is synthesized in almost all tissues of plants in the presence of oxygen (Yip, et al. (1988) *Plant Physiol* 88, 553-558). Ethylene biosynthesis involves 3 steps in plants. Methionine is catalyzed to form S-adenosylmethionine (S-AdoMet or SAM) by SAM synthetase. Biosynthesis of ethylene is committed by the conversion of SAM to 1-aminocyclopropane-1-carboxylic acid (ACC) by ACC synthase (ACS) (Yang, et al. (1984) *Annual Review of Plant physiology* 35, 155-189). ACC is subsequently oxidized to ethylene by ACC oxidase (ACO). Although ACO is constitutively expressed and can be further induced by wounding and ethylene (Barry, et al. (1996) *Plant J* 9, 525-535; English, et al. (1995) *Plant Physiol* 109, 1435-1440), the basal activity of ACS is extremely low unless induced by stress signals or at certain developmental stages (Tsuchisaka, et al. (2004) *Plant Physiol* 136, 2982-3000). Therefore, ACS appears to catalyze the rate-limiting step in ethylene biosynthesis, which is a highly regulated process in higher plant species (Yang, et al. (1984) *Annual Review of Plant physiology* 35, 155-189). All of the enzymes involved in ethylene biosynthesis, including SAM synthetase, ACC synthase, and ACC oxidase, are encoded by gene families, which suggests a complex and multi-layered regulation of ethylene emanation (Lin, et al. (2009) *J Exp Bot* 60, 3311-3336).

Genetic mutants defective in the regulation of ethylene biosynthesis have been identified in *Arabidopsis* (Guzman, et al. (1990) *Plant Cell* 2, 513-523; Roman, et al. (1995) *Genetics* 139, 1393-1409). In etiolated seedlings, three ethylene overproduces (eto) mutants, eto1, eto2 and eto3, produce ethylene ranging from 5- to 50-fold higher than that in wild-type *Arabidopsis* (Guzman, et al. (1990) *Plant Cell* 2, 513-523; Chae, et al. (2003) *Plant Cell* 15, 545-559). *Arabidopsis* ETO2 and ETO3 encode ACS5 and ACS9, two isoforms of type 2 ACS in the gene family (Chae, et al. (2003) *Plant Cell* 15, 545-559; Vogel, et al. (1998) *Proc Natl Acad Sci USA* 95, 4766-4771; Yoshida, et al. (2005) *BMC Plant Biol* 5, 14). ETO1 binds type 2 ACS proteins and interacts with CUL3 in the SCF ubiquitin E3 ligase (Yoshida, et al. (2005) *BMC Plant Biol* 5, 14; Christians, et al. (2009) *Plant J* 57, 332-345; Thomann, et al. (2005) *FEBS Lett* 579, 3239-3245; Wang, et al. (2004) *Nature* 428, 945-950). ETO1 and ETO1-like (EOL) proteins regulate the protein stability of ETO2/ACS5 and ETO3/ACS9 by the ubiquitin-proteasome pathway (Christians, et al. (2009) *Plant J* 57, 332-345; Wang, et al. (2004) *Nature* 428, 945-950). Hypermorphic mutations in eto2-1 and eto3-1 disrupt the protein interactions of ACS5 and ACS9, respectively, with ETO1 resulting in an elevated ACS activity and subsequent ethylene overproduction, which phenocopies the loss-of-function mutations in ETO1 (Guzman, et al. (1990) *Plant Cell* 2, 513-523; Chae, et al. (2003) *Plant Cell* 15, 545-559; Vogel, et al. (1998) *Proc Natl Acad Sci USA* 95, 4766-4771). How the protein-protein interaction between ETO1 and type 2 ACS is regulated by internal and external signals to mediate ethylene production remains largely unclear.

Chemical screening of small molecules as modulators in biological processes of clinically important proteins has been intensively applied in drug discovery (Knight, et al. (2007) *Cell* 128, 425-430). Small molecules offer advantages of reversible, conditional and rapid effects for functional studies in organisms in which lethality is a critical issue in genetic mutants. In a sense, plant hormones are small molecules that function as bioactive compounds to modulate plant physiology. Chemical genetics has been recently appreciated as a novel methodology to probe plant physiology in *Arabidopsis* by combining chemical screening and genetics approaches (Blackwell, et al. (2003) *Plant Physiol* 133, 448-455; Toth, et al. (2010) *Trends Plant Sci* 15, 81-88).

SUMMARY OF THE INVENTION

The present invention provides methods of improving the quality of harvested plants comprising providing to said plants an effective amount of a compound of formula I:

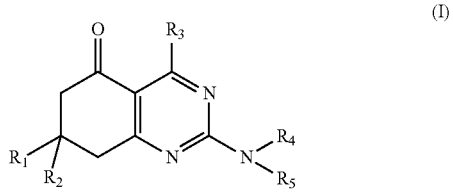

wherein $R_1$, $R_2$, and $R_3$ independently are H, optionally substituted $C_1$-$C_8$ alkyl, optionally substituted aryl, or optional substituted heteroaryl; and $R_4$ and $R_5$ independently are H, optionally substituted $C_1$-$C_8$ alkyl, optionally substituted cycloalkyl, optionally substituted aryl, or optional substituted heteroaryl.

In another aspect, the present invention also provides compounds for inhibiting 1-aminocyclopropane-1-carboxylate synthase in a plant, wherein the compounds have the structure of formula I:

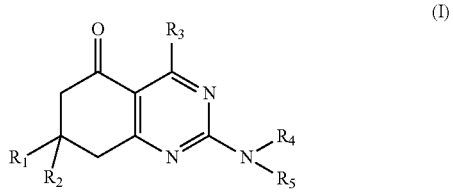

wherein $R_1$, $R_2$, and $R_3$ independently are H, optionally substituted $C_1$-$C_8$ alkyl, optionally substituted aryl, or optional substituted heteroaryl;

$R_4$ and $R_5$ independently are H, optionally substituted $C_1$-$C_8$ alkyl, optionally substituted cycloalkyl, optionally substituted aryl, or optional substituted heteroaryl.

INCORPORATION BY REFERENCE

All publications, patents, and patent applications mentioned in this specification are herein incorporated by reference for the purposes cited, to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

(FIG. 1A) A schematic representation of strategy for chemical screening. Seeds of 5×EBS::LUC in eto1-4 were sown on 0.5×MS agar medium containing 50 or 25 µM small molecules. Suppression of triple response phenotype was scored 3 days after germination in the dark, and the number of candidate compounds from 3 rounds of chemical screening is indicated. (FIG. 1B) Suppression of eto1-4 phenotype by 3 exemplary invention compounds (9393, 9370, and 7303) at 10 µM. Wild type (WT) and eto1-4 were germinated in the dark for 3 days before scoring the phenotype in the presence of the exemplary invention compounds or silver thiosulfate (STS). (FIG. 1C) Suppression of luciferase activity in the seedlings of 5×EBS::LUC (eto1-4) by the exemplary invention compounds. Images in pseudocolor represent luciferase activity in the presence of 10 µM of the exemplary invention compounds, STS or aminoethoxyvinylglycine (AVG). DMSO was used as solvent for chemicals and control. (FIG. 1D) The exemplary invention compounds reduced the elevated ethylene level in etiolated eto1-4. Ethylene levels were quantitated by gas chromatography (GC) from the headspace of 20-mL GC vials with 3-day-old etiolated seedlings. Data are means from at least 3 replicates (n>30 each vial). Error bars indicate SE.

(FIG. 6A)

Exemplary invention compounds reduce the enzyme activity of ACC synthase in vitro. Purified recombinant ACS5 was incubated with different concentrations of exemplary invention compounds and AVG in 20-mL GC vials for in vitro activity assay (Experimental Procedures) Activity unit was defined as 1 µmol ACC converted by 1 µg ACS5 in 30 min at 25° C. (FIG. 6B) Lineweaver-Burk plot of ACS5 kinetic data in the presence of AVG and compound 7303 as inhibitors (I) is shown. Different concentrations of SAM were incubated with AVG and compound 7303 at 0.05 and 0.1 µM for in vitro activity assay (Experimental Procedures). Data are means from at least 3 duplicates and the experiments were repeated twice with similar results. A representative result is shown in FIG. 6A and FIG. 6B, respectively. Error bars indicate SE.

(FIG. 7A) Hierarchical clustering of expression profiles in wild type (Col-0) and eto1-4 treated with or without the exemplary invention compounds. The sample raw data were filtered and normalized by all sample medium, and the genes with expression levels counted as present calls from 2 biological duplicates were selected for analysis by Bioconductor, exemplary map program in marray package. The master gene pool for clustering analysis consisted of 1,446 genes from the whole genome with at least 1.5-fold difference in expression levels between 3-day-old etiolated wild type and eto1-4 seedlings. Venn diagrams show the number of genes co-regulated by AVG and individual exemplary invention compounds (FIG. 7B); by AVG and all of the exemplary invention compounds (FIG. 7C). Percentages of co-regulated genes in FIG. 7B were indicated as AVG dependent (63.4%, 69.3% and 71.1%) and independent (43.4%, 46.5% and 38.6%) groups.

DETAILED DESCRIPTION OF THE INVENTION

Figure 1A:
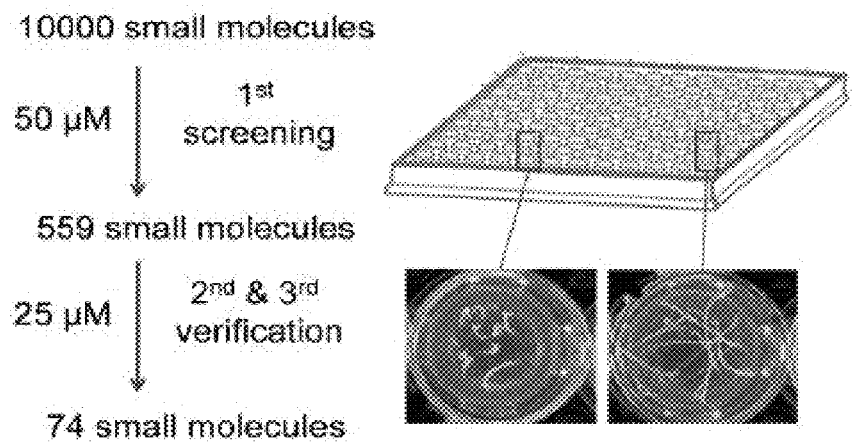
FIG. 1A-1D illustrate process and results of chemical screening for antagonists of ethylene response in etiolated *Arabidopsis* seedlings.

Ethylene is a gaseous hormone important for adaptation and survival in plants. To further understand the signaling and regulatory network of ethylene, a phenotype-based screening strategy was used to identify chemical compounds interfering with the ethylene response in *Arabidopsis thaliana*. By screening a collection of 10,000 structurally diverse small molecules, several exemplary invention compounds suppressing the constitutive triple response phenotype in the ethylene overproducer mutant eto1-4 were identified. The exemplary invention compounds reduced the expression of a reporter gene responsive to ethylene and the otherwise elevated level of ethylene in eto1-4. Structural and functional analysis revealed that the exemplary invention compounds contain a quinazolinone backbone. Further studies with genetic mutants and transgenic plants involved in the ethylene pathway revealed that the exemplary invention compounds inhibit ethylene biosynthesis at the step of converting S-adenosylmethionine to 1-aminocyclopropane-1-carboxylic acid (ACC) by ACC synthase. Biochemical studies with in vitro activity assay and enzyme kinetics analysis indicated that a representative exemplary compound was an uncompetitive inhibitor of ACC synthase. Finally, global gene expression profiling uncovered a significant number of genes that were co-regulated by the exemplary invention compounds and aminoethoxyvinylglycine, a potent inhibitor of ACC synthase. The use of chemical screening is effective in identifying small molecules modulating the ethylene response in *Arabidopsis* seedlings. Discovery of such chemical compounds will be useful in ethylene research and will offer potentially useful agrochemicals for quality improvement in harvested agriculture.

By using a phenotype-based strategy, several small molecules suppressing the constitutive triple response phenotype in etiolated eto1 seedlings by interfering with the biosynthesis but not the signaling transduction of ethylene were identified. Using an in vitro activity assay, it was demonstrated that the invention molecules are inhibitors of ACS enzymes. Further enzymatic analysis revealed that the exemplary invention compounds are novel ACS inhibitors different from the well-known aminoethoxyvinylglycine (AVG). In addition, global gene expression analysis supports the physiological role of the invention small molecules in the ethylene response by reverting the expression of almost 50% of differentially expressed genes in eto1-4 to the levels of wild-type plants.

Unless defined otherwise, all technical and scientific terms used herein have the standard meaning pertaining to the claimed subject matter belongs. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The term "alkyl" as used herein, means a straight, branched chain, or cyclic (in this case, it would also be known as "cycloalkyl") hydrocarbon containing from 1-10 carbon atoms. Illustrative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term "$C_1$-$C_6$-alkyl" as used herein, means a straight, branched chain, or cyclic (in this case, it would also be known as "cycloalkyl") hydrocarbon containing from 1-6 carbon atoms. Representative examples of alkyl include, but are not limited to, methyl, ethyl, n-propyl, iso-propyl, cyclopyl, n-butyl, sec-butyl, tert-butyl, cyclobutyl, n-pentyl, isopentyl, neopentyl, cyclopentyl, and n-hexyl.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

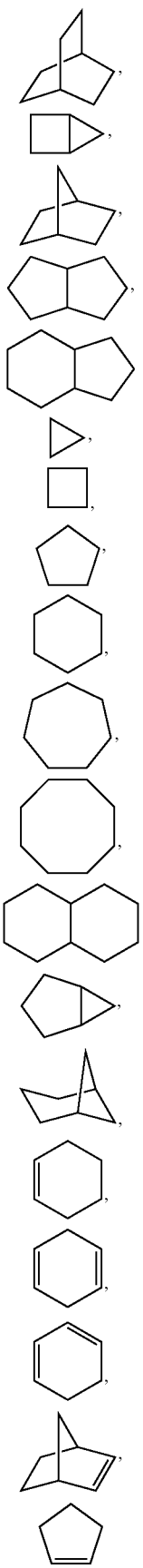

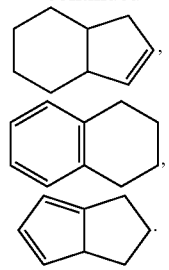

In some embodiments, depending on the structure, a cycloalkyl group is a monoradical or a diradical (e.g., a cycloalkylene group).

The term "aromatic" as used herein, refers to a planar ring having a delocalized π-electron system containing 4n+2π electrons, where n is an integer. In some embodiments, aromatic rings are formed by five, six, seven, eight, nine, or more than nine atoms. In other embodiments, aromatics are optionally substituted. The term includes monocyclic or fused-ring polycyclic (i.e., rings which share adjacent pairs of carbon atoms) groups.

The term "aryl" as used herein, refers to an aromatic ring wherein each of the atoms forming the ring is a carbon atom. In some embodiments, aryl rings are formed by five, six, seven, eight, nine, or more than nine carbon atoms. Examples of aryl groups include, but are not limited to phenyl, naphthalenyl, phenanthrenyl, anthracenyl, fluorenyl, and indenyl.

In some embodiments, the term "aryl" as used herein means an aryl group that is optionally substituted with one, two, three, four or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carbonyl, cyano, formyl, haloalkoxy, haloalkyl, halogen, hydroxyl, hydroxyalkylene, mercapto, nitro, —NR$_A$R$_A$, and (NR$_A$R$_B$)carbonyl.

The term "halo" or "halogen" as used herein, means a —Cl, —Br, —I or —F.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In some embodiments, the polycyclic heteroaryl group is fused or non-fused. Illustrative of heteroaryl groups include, but are not limited to, the following moieties:

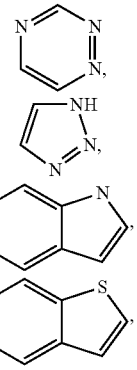

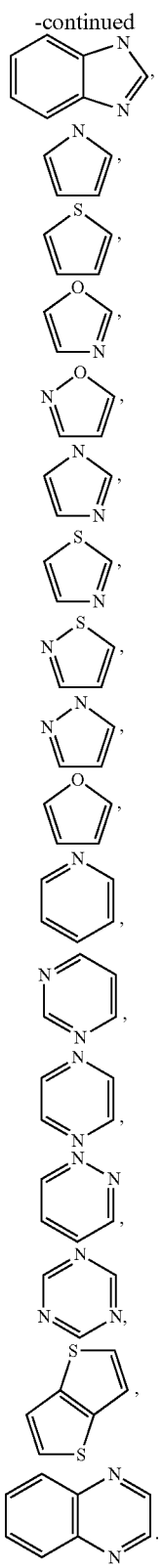

In some embodiments, depending on the structure, a heteroaryl group is a monoradical or a diradical (i.e., a heteroarylene group).

The term "heteroaryl" means heteroaryl groups that are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkylene, mercapto, nitro, —NR$_A$R$_B$, and —(NR$_A$R$_B$)carbonyl.

The term "substituted" means that the referenced group is optionally substituted (substituted or unsubstituted) with one or more additional group(s) individually and independently selected from alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. By way of example an optional substituents is L$_s$R$_s$, wherein each L$_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each R$_s$ is independently selected from H, (substituted or unsubstituted lower alkyl), (substituted or unsubstituted lower cycloalkyl), heteroaryl, or heteroalkyl.

The term "optionally substituted" as defined herein, means the referenced group is substituted with zero, one or more substituents as defined herein.

Throughout the specification, groups and substituents thereof are chosen, in certain embodiments, to provide stable moieties and compounds.

Unless otherwise indicated, conventional methods of mass spectroscopy, NMR, HPLC, protein chemistry, biochemistry, recombinant DNA techniques and pharmacology are employed. Unless specific definitions are provided, the standard nomenclature employed in connection with, and the standard laboratory procedures and techniques of, analytical chemistry, synthetic organic chemistry, and medicinal and pharmaceutical chemistry are employed. In certain instances, standard techniques are used for chemical syntheses, chemical analyses, pharmaceutical preparation, formulation, and delivery, and treatment of patients. In certain embodiments, standard techniques are used for recombinant DNA, oligonucleotide synthesis, and tissue culture and transformation (e.g., electroporation, lipofection). In some embodiments, reactions and purification techniques are performed e.g., using kits of manufacturer's specifications or as commonly accomplished or as described herein.

In some embodiments provide methods for improving the quality of harvested plants comprising providing to said plants an effective amount of a compound of formula I:

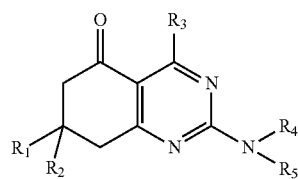

(I)

wherein
R$_1$, R$_2$, and R$_3$ independently are H, optionally substituted C$_1$-C$_8$ alkyl, optionally substituted aryl, or optional substituted heteroaryl;
R$_4$ and R$_5$ independently are H, optionally substituted C$_1$-C$_8$ alkyl, optionally substituted cycloalkyl. In some embodiments, $R_1$ is H or optionally substituted $C_1$-$C_8$ alkyl. For example, $R_1$ is methyl, ethyl, propyl, butyl, pentyl, and the like. In other embodiments, $R_1$ is optionally substituted aryl, or optional substituted heteroaryl. In certain embodiments, $R_1$ is optionally substituted phenyl. In certain embodiments, $R_1$ is optionally substituted pyridine, piperidine, or the like. In some embodiments, $R_2$ is H or optionally substituted $C_1$-$C_8$ alkyl. For example, $R_2$ is methyl, ethyl, propyl, butyl, pentyl, and the like. In other embodiments, $R_2$ is optionally substituted aryl, or optional substituted heteroaryl. In certain embodiments, $R_2$ is optionally substituted phenyl. In certain embodiments, $R_2$ is optionally substituted pyridine, piperidine, or the like. In some embodiments, $R_1$ is H and $R_2$ is optionally substituted phenyl. In certain embodiments, the phenyl is substituted with alkoxy, halogen, or $C_1$-$C_8$ alkyl. In certain embodiments, the phenyl is substituted with methoxy, ethoxy, propoxy, and the like. In certain embodiments, the phenyl is substituted with F, Cl, Br, or I. In certain embodiments, the phenyl is substituted with methyl, ethyl, propyl, butyl, pentyl, and the like. In other embodiments, $R_1$ and $R_2$ independently are optionally substituted $C_1$-$C_8$ alkyl or H. In certain embodiments, $R_1$ and $R_2$ independently are $CH_3$ or H. In some embodiments, $R_1$ is $CH_3$ and $R_2$ is $CH_3$. In some embodiments, $R_3$ is optionally substituted $C_1$-$C_8$ alkyl. In other embodiments, $R_3$ is H, methyl, ethyl, or n-propyl.

In some embodiments, methods for improving the quality of harvested plants comprising providing to the plants an effective amount of a compound of formula I to the leaves, buds fruits and/or flowers of the plants. In other embodiments, the compound is applied to the roots of the plants.

The exemplary invention compounds are providing to the plants by e.g., applying to plants by either sparing, the leaves, buds, fruits, flowers and/or roots or by "drenching." When applied by spraying, the compounds are spraying on the plants, for example to the point of runoff, by techniques known in the art.

In some embodiments, the invention compounds are formulated to compositions comprising an appropriate carrier. In certain embodiments, the carrier comprises an anionic or non-ionic surfactant to aid in thoroughly wetting the plants. In the drenching method, the invention compounds in a suitable formulations are poured into the soil surrounding the plants or can be applied to the roots from below follows any known techniques in the art.

In some embodiments, the improved quality of harvested plants is maintaining the freshness and quality of leaves, buds, fruits and/or flowers after harvest. In certain embodiments, the improved quality of harvested plants is maintaining the freshness of leaves, buds, fruits and/or flowers after harvest. In certain embodiments, the improved quality of harvested plants is maintaining the quality of leaves, buds, fruits and/or flowers after harvest. In other embodiments, the improved quality of harvested plants is prolonging the vase life of cut leaves, buds and/or flowers. In these applications, the method can be used by commercial wholesale florists to harvest flower crops earlier. In addition, the beneficial effects, such as the increase in flower longevity, accompanying the application of the exemplary invention compounds to the flowering plants carry over to the cut flowers after harvesting.

In some embodiments provide harvested plants that have been provided with the invention compounds or compositions comprising invention compounds. The invention harvested plants (including any parts of the plants, e.g., leaves, buds, fruits and/or flowers) maintain the freshness or quality of leaves, buds, fruits and/or flowers after harvest. In some instances, the invention harvested plants prolong the vase life of cut leaves, buds and/or flowers.

In some embodiments provide compounds inhibiting 1-aminocyclopropane-1-carboxylate synthase in a plant, wherein the compounds have the structure of formula I:

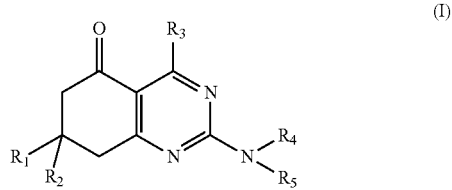

wherein
$R_1$, $R_2$, and $R_3$ independently are H, optionally substituted $C_1$-$C_8$ alkyl, optionally substituted aryl, or optional substituted heteroaryl; and
$R_4$ and $R_5$ independently are H, optionally substituted $C_1$-$C_8$ alkyl, optionally substituted cycloalkyl.

In some embodiments, $R_1$ is H or optionally substituted $C_1$-$C_8$ alkyl. For example, $R_1$ is methyl, ethyl, propyl, butyl, pentyl, and the like. In other embodiments, $R_1$ is optionally substituted aryl, or optional substituted heteroaryl. In certain embodiments, $R_1$ is optionally substituted phenyl. In certain embodiments, $R_1$ is optionally substituted pyridine, piperidine, or the like. In some embodiments, $R_2$ is H or optionally substituted $C_1$-$C_8$ alkyl. For example, $R_2$ is methyl, ethyl, propyl, butyl, pentyl, and the like. In other embodiments, $R_2$ is optionally substituted aryl, or optional substituted heteroaryl. In certain embodiments, $R_2$ is optionally substituted phenyl. In certain embodiments, $R_2$ is optionally substituted pyridine, piperidine, or the like. In some embodiments, $R_1$ is H and $R_2$ is optionally substituted phenyl. In certain embodiments, the phenyl is substituted with alkoxy, halogen, or $C_1$-$C_8$ alkyl. In certain embodiments, the phenyl is substituted with methoxy, ethoxy, propoxy, and the like. In certain embodiments, the phenyl is substituted with F, Cl, Br, or I. In certain embodiments, the phenyl is substituted with methyl, ethyl, propyl, butyl, pentyl, and the like. In other embodiments, $R_1$ and $R_2$ independently are optionally substituted $C_1$-$C_8$ alkyl or H. In certain embodiments, $R_1$ and $R_2$ independently are $CH_3$ or H. In some embodiments, $R_1$ is $CH_3$ and $R_2$ is $CH_3$. In some embodiments, $R_3$ is optionally substituted $C_1$-$C_8$ alkyl. In other embodiments, $R_3$ is H, methyl, ethyl, or n-propyl.

The present invention provides exemplary invention small molecules that interfere with the ethylene response in *Arabidopsis*. Conventional genetic studies of primarily *Arabidopsis* mutants to uncover the key components to establish the ethylene pathway in a hierarchical manner have laid the foundation to understand how the ethylene response is initiated and transduced. Here, an invention approach was demonstrated by using a combination of ethylene mutants and chemical screening to further explore the ethylene pathway in plants. The present invention has identified structurally related quinazolinones as the exemplary invention compounds (Table 1), which function as ethylene antagonists from phenotype-based screening. Further characterization of the exemplary invention compounds revealed that these small molecules are novel inhibitors of ACC synthase in suppressing ethylene biosynthesis in an uncompetitive fashion and offers potential applications in harvested management.

Eto1-4 for phenotype-based chemical screening was used to identify exemplary invention compounds that interfere with the ethylene response, which may take place at any steps downstream of the conversion of SAM to ACC by ACC synthase in the ethylene biosynthetic pathway. However, the identified exemplary invention compounds affect only the ethylene biosynthesis but not the signaling pathway to completely suppress the triple response phenotype in etiolated eto1-4. There were no significant difference found between eto2-1 and eto1-4 in the hypocotyl phenotype, despite eto2-1 produced nearly 5 times the ethylene as eto1-4 (FIG. 5) Although 10 µM of the exemplary invention compounds completely suppressed the ethylene emanation and hypocotyl phenotype in eto1-4, it produced only 25% of the suppression in hypocotyl length in eto2-1 even with 30 µM of the most effective compound, 7303. This finding indicates that the severity of the mutant phenotype and the potency of compounds will determine the outcome of phenotype-based chemical screening. Despite the potency of AVG in inhibiting ethylene biosynthesis, increasing concentrations of AVG still did not completely suppress the hypocotyl phenotype in eto2-1 as compared with eto1-4, although the ethylene production in both mutants was reduced to a comparable level (See FIG. 5). The hypocotyl phenotype in eto2-1 may not be entirely dependent on overproduced ethylene, and thus not be completely affected by the exemplary invention compounds.

In some embodiments, distinct mechanisms of AVG and the exemplary invention compounds in inhibiting ACC synthase contribute to their effectiveness in suppressing ethylene production. ACC synthase is a PLP-dependent enzyme and related to aminotransferases (Yang, et al. (1984) *Annual Review of Plant physiology* 35, 155-189; Eliot, et al. (2004) *Annu Rev Biochem* 73, 383-415). AVG is a competitive inhibitor that competes with SAM for the catalytic site of ACC synthase (Boller, et al. (1979) *Planta* 145, 293-303; Hyodo, et al. (1986) *Plant Cell Physiol.* 27, 391-398). In addition, crystal structure studies of ACC synthase from apple and tomato provided atomic details to propose the chemical interactions of PLP and AVG in the active site of ACS enzymes (Capitani, et al. (2002) J Biol Chem 277, 49735-49742; Capitani, et al. (2005) FEBS Lett 579, 2458-2462; Huai, et al. (2001) J Biol Chem 276, 38210-38216). A stable ketimine structure was formed by AVG interacting with PLP in ACC synthase and thus presented unfavorable catalytic sites to accommodate SAM as a substrate (Capitani, et al. (2002) J Biol Chem 277, 49735-49742). Unlike AVG, compound 7303 displayed an uncompetitive inhibition, whereby the inhibitor interacted with an enzyme-substrate (E-S) complex instead of enzyme (E) alone to abrogate product formation. The kinetic parameters of enzymes such as Km and Vmax are both reduced in uncompetitive inhibition. Since Km is the measure of affinity between substrates and enzymes, the reduced Km corresponds to a higher affinity in the presence of uncompetitive inhibitors. This intriguing phenomenon occurs because the equilibrium is shifted to form an E-S complex due to binding of the inhibitor (I) to E-S to form the unproductive E-S-I complex, which results in decreased concentration of the E-S complex. Results from enzyme kinetic studies indicated that the Km and Vmax of recombinant ACS5 were decreased from 54.8±7.8 to 37.1±2.9 µM and 95.1±5.0 to 50.5±1.2 µM, respectively, in the presence of 0.1 µM of compound 7303 (from data prepared for FIG. 6B), which supports the categorization by the Lineweaver-Burk plot of the exemplary compound as uncompetitive inhibitors. Because AVG can interact with PLP to form an inhibitory adduct, that AVG is also an inhibitor of PLP-dependent enzymes (Clausen, et al. (1997) Biochemistry 36, 12633-12643; Krupka, et al. (2000) EMBO J 19, 3168-3178) is not surprising. However, the exemplary invention exemplary invention compounds identified herein are unlikely general inhibitors of PLP-dependent enzymes.

The exemplary invention compounds found herein effectively inhibited ACC synthase activity in vitro and suppressed ethylene production in eto 1-4 seedlings. The potency of the exemplary invention compounds differs. To understand the physiological impact of exemplary invention compounds at the gene expression level, DNA microarray methodology was used to examine the gene expression patterns regulated by the exemplary invention compounds compared with that by AVG. Approximately 43% to 50% of 1,446 genes differentially expressed in eto1-4 and WT were regulated by the individual exemplary invention compounds, as compared with almost 39% by AVG. The hierarchical clustering of expression profiles from 1,446 genes also suggested genes regulated by the exemplary invention compounds but not dependent on ethylene response. The exemplary invention compounds have functions other than regulation of ethylene biosynthesis and response. Previous transcriptome studies of ethylene responsive genes focused on those differentially regulated by ethylene treatment within a short time (Goda, et al. (2008) *Plant J* 55, 526-542; Nemhauser, et al. (2006) *Cell* 126, 467-475), and the genes identified from those experiments would likely be the immediate targets specific to ethylene induction. However, the 276 genes identified herein by microarray analysis resulted from differential expression in 3-day-old etiolated seedlings of WT and eto1-4 mutant and may not be the immediate ethylene responsive genes but instead represent a regulation network leading to triple response induced by endogenously elevated ethylene. Only 39 out of the 276 genes were identical to previous data acquired from transient induction by ethylene, which indicates a difference in sustained and immediate response to ethylene (Nemhauser, et al. (2006) *Cell* 126, 467-475). Since the 276 co-regulated genes by AVG and exemplary invention compounds were selected from the 1,446 genes differentially expressed in WT and eto1-4, further analysis to study the functions of these genes would provide useful information to dissect how ethylene triggers the triple response phenotype during etiolated growth.

On mutant screening, the newly identified exemplary invention compounds were found endowed with potential to identify new components in the ethylene pathway. Combining both genetics and biochemistry approaches to characterize the biological property of exemplary invention compounds demonstrates an effective platform to identify useful chemicals in ethylene research.

EXAMPLE

Experimental Procedures

Plant Materials and Growth Condition

All mutants and transgenic plants were derived from the wild-type *Arabidopsis thaliana* Columbia ecotype (Col-0) and cultivated under a long-day condition (16-h light/8-h dark at 22° C.) under exemplary e light (100-150 µE $m^{-2}$ $s^{-1}$). A reporter construct, 5×EBS::LUC (a generous gift from Drs. Hai Li and Anna N. Stepanova, Salk Institute, USA), containing 5 copies of EIN3 binding sequence (EBS) fused with luciferase gene (LUC) was transformed to eto1-4 and subsequently used for screening compounds of a chemical library. Ethylene mutants eto1-4, eto2-1, ctr1-1 and the EIN3 overexpression line (35S::EIN3) were described previously (Solano, et al. (1998) *Genes Dev* 12, 3703-3714). Seeds were sterilized with 30% bleach for 6 min and sown in half-strength Murashige and Skoog (0.5×MS) medium supplemented with 0.8% agar and stratified in the dark at 4° C. for 3-4 days before germination. For analysis of the triple response phenotype, stratified seeds were grown in the dark at 22° C. for 3 days before scoring the phenotype.

Chemicals and Screening Procedure

A DIVERSet library (ChemBridge Inc.) containing 10,000 small molecules (in DMSO) was used for chemical screening. Three rounds of chemical screenings were carried out in 0.5×MS agar medium containing individual chemicals in each well of 96- and 24-well micro-titer plates. The initial screening was performed by sowing 10 to 15 seeds in the wells of micro-titer plates containing small molecules at 50 µM to score the long-hypocotyl phenotype. For the second and third screenings, we used 25 µM of small molecules selected from the first round of screening to score and confirm the phenotype. The seedling phenotype was scored by use of a digital camera attached to a Zeiss stereomicroscope (Ste-REO V8), and quantitation of hypocotyl length was performed by use of NIH Image J software. AVG and silver thiosulfate (STS, by mixing silver nitrate and sodium thiosulfate at a 1:4 molar ratio immediately before use) were obtained from Sigma and used as controls to suppress ethylene biosynthesis and perception, respectively. Agar medium was supplemented with 1-aminocyclopropane-1-carboxylic acid (10 µM, Merck) to induce the triple response in etiolated seedlings.

For live imaging of luciferase activity, plants were first grown in the dark at 22° C. for 3 days, then under exemplary e light for 3 more days before the luciference of seedlings was imaged. Six-day-old seedlings were sprayed with luciferin (2 µM, Biosynth International Inc.) and kept in the dark for 5 min before collecting images by the Xenogen IVIS System (Caliper Life Sciences, Inc.). For quantitative assay of luciferase activity, the etiolated seedlings mentioned above were transferred to exemplary e micro-titer plates (Packard Optiplate-96, Perkin Elmer Inc.) for an additional 3 days under exemplary e light in 0.5×MS solution. The luciferase activity of seedlings was quantitated by use of a microplate reader (CHAMELEON, Hidex Inc.) in the presence of 2 µM luciferin.

Protein Expression and Purification

The full-length cDNA of *Arabidopsis* ACS5 (At5g65800) was cloned to pETDuet (Novagen) to generate pETDuet-6His-ACS5 for expression in *E. coli* (BL21-CodonPlus, Stratagene) and subsequent purification of the recombinant ACS5 protein. Protein expression was induced at $OD_{600}$ 0.6 by adding 0.4 mM IPTG, and cells were incubated at 16° C. for 18 h. Cells were harvested by centrifugation at 6000×g for 10 min at 4° C. The cell pellet was washed and suspended in 50 mL phosphate buffer (300 mM NaCl, 20 mM phosphate buffer, pH 7.4) containing 20 mM imidazole. Cell lysis was achieved by a continuous high-pressure cell disrupter (TS 2.2 KW, Constant System) with 30 KPsi at 4° C. After washing the cell disrupter twice with 50 ml phosphate buffer containing 20 mM imidazole, the final 150 ml suspension was centrifuged at 10000×g for 30 min at 4° C. The supernatant was applied to a 5-mL HisTrap FF column in an AKTAprime system (GE Healthcare) and was subsequently washed stepwise with 100 mL buffer A (1 mM EDTA, 5 mM DTT, 250 mM HEPES buffer, pH 8.0) containing 20 mM imidazole, then 100 mL buffer A containing 100 mM imidazole. The bound protein was eluted by a 0.1-1.0 M gradient of imidazole in 25 mL buffer A and stored at −80° C. until further analysis.

Enzyme Activity and Kinetic Assays—In Vitro

Figure 8:
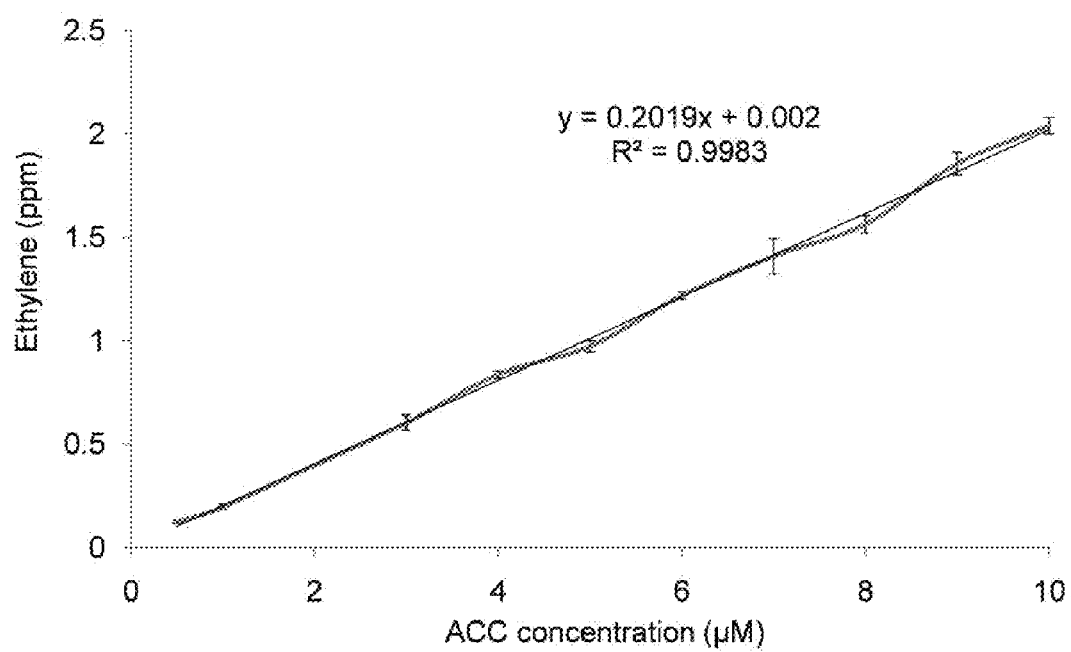
FIG. 8 provides standard curve that demonstrates correlation between ACC concentrations and ethylene levels. Different concentrations of ACC were used to chemically convert to ethylene in sealed GC vials. Ethylene levels were measured by GC to build up the standard curve for enzyme activity indicated in FIG. 5A.

ACS activity assay was performed as described (Lizada, et al. (1979) *Anal Biochem* 100, 140-145; Yamagami, et al. (2003) *J Biol Chem* 278, 49102-49112), with minor modifications. Purified ACS5 protein in 2 mL buffer A containing 10 µM pyridoxal 5′-phosphate (PLP) was mixed with test small molecules to a final concentration of 10 µM or DMSO (as control) in 20-mL GC vials on ice for 10 min followed by adding substrate to continue reactions for 30 min at 25° C. The strong oxidant $HgCl_2$ (100 µL, 20 mM) and NaOH: bleach (1:1, 100 µL) was added to the vials to stop reactions and to oxidize ACC to ethylene, which continued for 10 min on ice. Ethylene level was measured by use of a gas chromatograph (HP 6890, Hewlett-Packard) equipped with a capillary column (19095P-U04, Agilent Technologies) and an autosampler (HP 7694, Agilent Technologies). A standard curve was prepared for the enzyme activity assay by replacing the enzyme and substrate with different concentrations of ACC (FIG. 8). All of the ACS activity assays were performed in replicates and repeated at least 3 times.

For the enzyme kinetics assay, different concentrations of SAM (20, 40, 60, 80, 100, 150, and 200 µM) were used to determine the Km and Vmax of purified recombinant ACS5. In addition, two concentrations, 0.05 and 0.1 µM, of AVG and compound 7303 were tested to determine the inhibition constant Ki. Reactions of enzyme kinetics assay were performed by first incubating chemical inhibitors or DMSO with different concentrations of SAM in 20-mL GC vials, then 1.6 µg purified ACS5 was added to initiate the enzyme reaction for 30 min at 25° C. Gas chromatography was used to quantitate the levels of ethylene chemically converted from ACC as described previously. Data analysis of enzyme kinetics assays and preparation of Lineweaver-Burk plots were done by SIG-MAPLOT (Systat Software Inc.).

Transcriptional Profiling Data and Analysis

For chemical treatments, seeds were sown on 0.5×MS agar medium supplemented with 10 µM chemicals (AVG, compounds 9393, 9370, and 7303) or DMSO (as control). *Arabidopsis* seeds were stratified in the dark at 4° C. for 4 days, then germinated in the dark for 3 days at 22° C. Approximately 2,000 etiolated seedlings of the wild type or eto1-4 were used to collect tissues for preparation of total RNA in each microarray experiment with *Arabidopsis* ATH1 GeneChip (Affymetrix). Extraction of RNA followed an established protocol (Chang, et al. (1993) *Plant Mol. Biol. Rep.* 11, 113-117). Total RNA (10 µg) was used to prepare biotinylated cRNA for hybridization to ATH1 GeneChip in the experiments disclosed herein. Experiments were repeated by 2 independent biological duplicates, and candidate genes present in both experiments were selected for further analysis. The MASS method was used for data analysis and normalization by all sample medium. Candidate genes were selected by the following criteria. First, genes with 1.5-fold differential expression between the wild type and eto1-4 were selected as the master gene pool, which was then used for comparison in treatments with AVG and individual exemplary compounds. Data were presented in hierarchical clustering and Venn diagram format. Agilent GeneSpring GX and Bioconductor software were used to analyze the expression profile data. Gene Ontology descriptions were generated by GeneSpring GX and further referred to the TAR GO database. Raw data are available in the GEO database (http://www.ncbi.nlm.nih.gov/geo) with Accession no. GSE20897.

Example 1

Figure 1B:
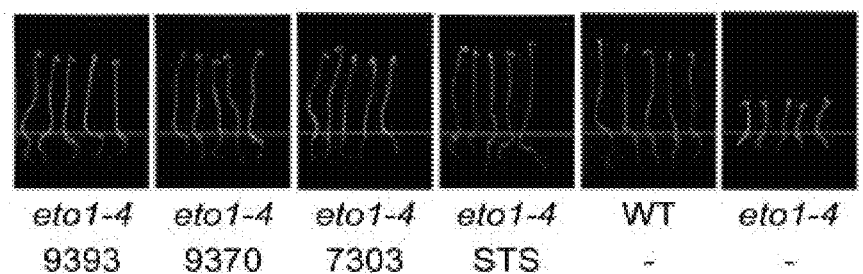

Phenotype-Based Screening for Chemical Compounds Interfering with Ethylene Response In this study, the chemical screening aimed to identify small molecules that interfered with the ethylene response in *A. thaliana*. A phenotype-based screening strategy was devised whereby *Arabidopsis* seedlings were germinated in micro-titer plates containing small molecules in individual wells. Several genetic mutants are available for the proposed screening, such as eto1-4, ctr1-1, and multiple ethylene receptor mutants that show constitutive triple response in etiolated seedlings (Guzman, et al. (1990) *Plant Cell* 2, 513-523; Kieber, et al. (1993) *Cell* 72, 427-441; Qu, et al. (2007) *BMC Plant Biol* 7, 3). Eto1-4 was used for chemical screening because its site of action is at the early step of ethylene response. Therefore, small molecules interfering with any step downstream of ACC formation could be screened. After screening 10,000 small molecules in DIVERSet by 3 consecutive cycles, 74 chemical compounds were identified effecting differential degrees of suppression of the triple response (FIG. 1A). For example, two chemical compounds, designated compounds 9393 and 9370 (Table 1) were found to demonstrate the effectiveness comparable to that of silver nitrate (in the form of silver thiosulfate, STS; Experimental Procedures) in suppressing the eto1-4 phenotype (FIG. 1B). Silver nitrate is an antagonist of ethylene receptors in blocking ethylene binding to suppress ethylene response. Compound 7303, was uncovered later by searching structural analogues; the compound showed the effect comparable to that of compounds 9393 and 9370 in suppressing the eto1-4 phenotype (FIGS. 1A and 1B). Compounds 9393, 9370 and 7303, among other exemplary invention compounds are highly effective in phenotypical assay.

TABLE 1

Exemplary invention compounds used herein.

Type I

| Compound | Structure |
|---|---|
| 7303 | |
| 2616 | |
| 8107 | |
| 9370 | 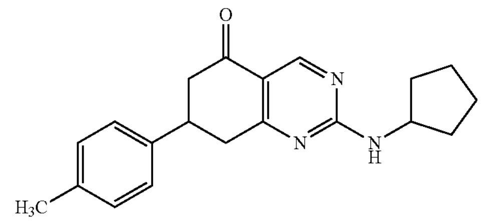 [SMILES: Cc1ccc(C2CC(=O)c3cnc(NC4CCCC4)nc3C2)cc1] |
| 8530 | 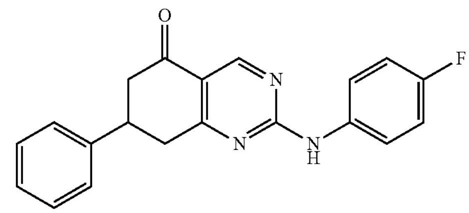 [SMILES: O=C1CC(c2ccccc2)Cc2nc(Nc3ccc(F)cc3)ncc21] |
| 0932 | 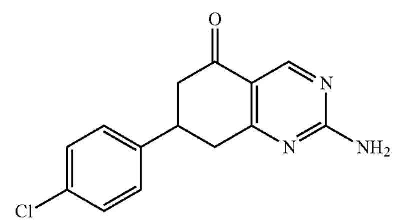 [SMILES: Nc1ncc2c(n1)CC(c1ccc(Cl)cc1)CC2=O] |
| 1560 | 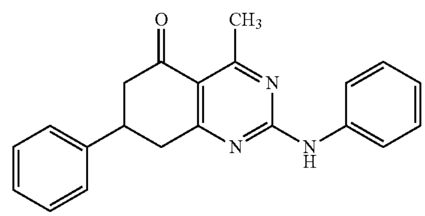 [SMILES: Cc1nc(Nc2ccccc2)nc2c1C(=O)CC(c1ccccc1)C2] |
| 1578 | 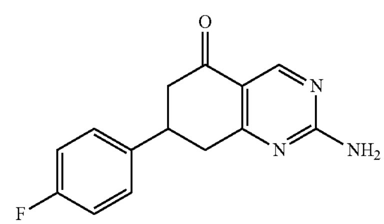 [SMILES: Nc1ncc2c(n1)CC(c1ccc(F)cc1)CC2=O] |
| 1682 | 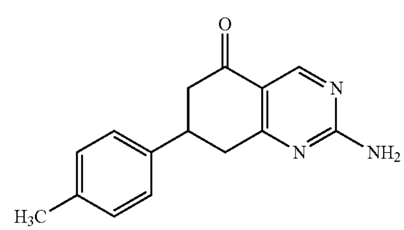 [SMILES: Cc1ccc(C2CC(=O)c3cnc(N)nc3C2)cc1] |
| 1713 | 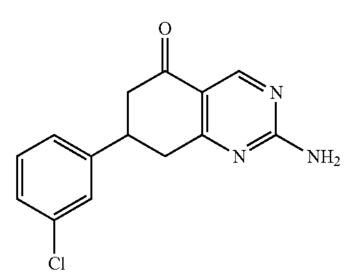 [SMILES: Nc1ncc2c(n1)CC(c1cccc(Cl)c1)CC2=O] |

TABLE 1-continued

| Compound | Structure |
|---|---|
| 3827 | 7-phenyl-2-(p-tolylamino)-7,8-dihydroquinazolin-5(6H)-one |
| 4752 | 2-amino-7-(o-tolyl)-7,8-dihydroquinazolin-5(6H)-one |

Type II

| Compound | Structure |
|---|---|
| 9393 | 2-(cyclopentylamino)-7,7-dimethyl-7,8-dihydroquinazolin-5(6H)-one |
| 2305 | 7-methyl-2-(phenylamino)-7,8-dihydroquinazolin-5(6H)-one |
| 9028 | 7,7-dimethyl-2-(phenylamino)-7,8-dihydroquinazolin-5(6H)-one |
| 9362 | 2-((4-fluorobenzyl)amino)-7,7-dimethyl-7,8-dihydroquinazolin-5(6H)-one |
| 5203 | 4,7,7-trimethyl-2-(phenylamino)-7,8-dihydroquinazolin-5(6H)-one |
| 5873 | 2-(benzylamino)-7-methyl-7,8-dihydroquinazolin-5(6H)-one |
| 4120 | 2-(benzylamino)-7,7-dimethyl-7,8-dihydroquinazolin-5(6H)-one |
| 0414 | 2-((4-fluorophenyl)amino)-7,7-dimethyl-7,8-dihydroquinazolin-5(6H)-one |
| 7336 | 2-amino-4-butyl-7,7-dimethyl-7,8-dihydroquinazolin-5(6H)-one |
| 8359 | 2-((4-fluorophenyl)amino)-4,7,7-trimethyl-7,8-dihydroquinazolin-5(6H)-one |
| 0093 | 2-((4-fluorophenyl)amino)-7-methyl-7,8-dihydroquinazolin-5(6H)-one |
| 5435 | 2-((4-ethylphenyl)amino)-7-methyl-7,8-dihydroquinazolin-5(6H)-one |
| 6405 | 7,7-dimethyl-2-(phenethylamino)-7,8-dihydroquinazolin-5(6H)-one |

TABLE 1-continued

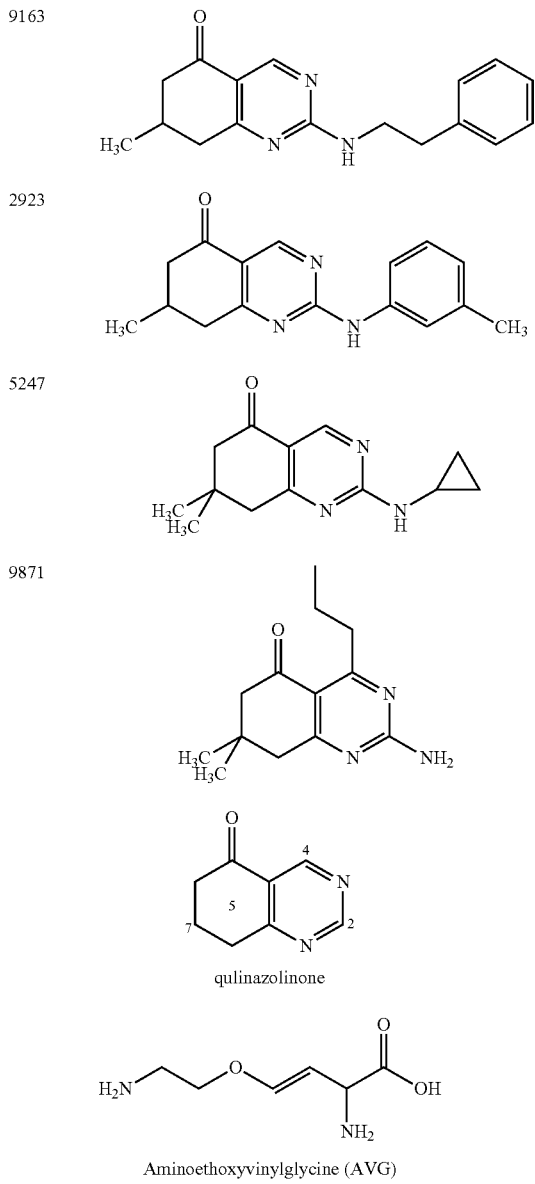

Figure 1C:
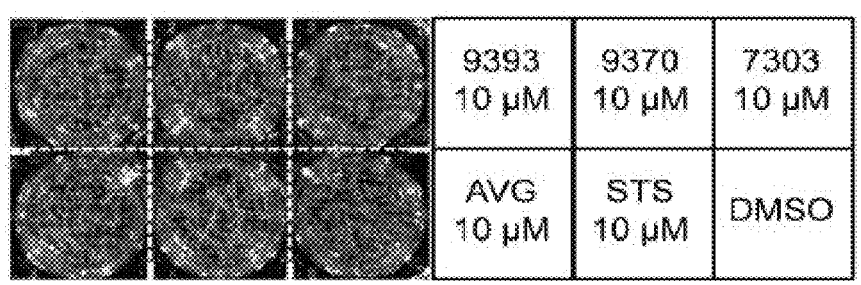
Figure 1D:
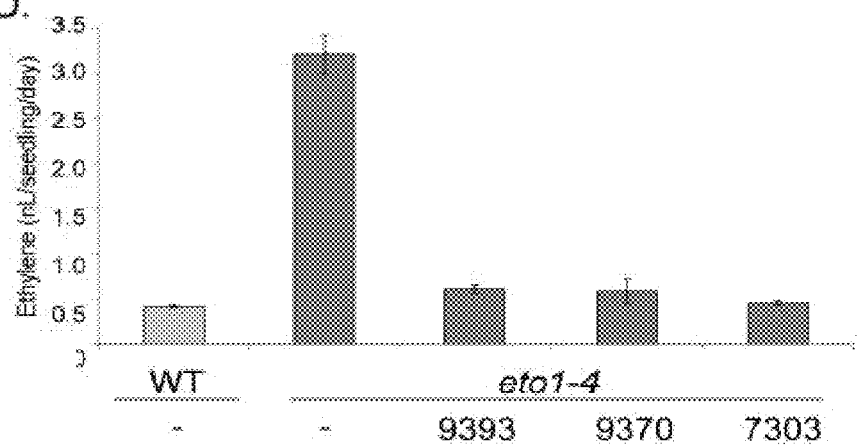

To confirm the suppression of the eto1-4 phenotype resulting from disruption of the ethylene response, the following assays were performed. First, luciferase activity was analyzed with a transgenic reporter line harboring 5 copies of a synthetic promoter fusion with a luciferase gene (LUC), 5×EBS::LUC, in the eto1-4 background. EBS represents the EIN3 binding sequence with the promoter activity of EBS induced by ethylene (Solano, et al. (1998) *Genes Dev* 12, 3703-3714; Yanagisawa, et al. (2003) *Nature* 425, 521-525). The luciferase activity of 5×EBS::LUC reporter was constitutively activated in eto1-4 but suppressed in the presence of STS, which indicates the expected ethylene responsiveness (FIG. 1C). AVG is an inhibitor of ACC synthase and many other pyridoxal enzymes that require PLP as the cofactor (Adams, et al. (1979) *Proc Natl Acad Sci USA* 76, 170-174; Eliot, et al. (2004) *Annu Rev Biochem* 73, 383-415). It was found that AVG also suppressed the luciferase activity like STS. In the presence of the exemplary invention compounds, the otherwise activated luciferase activity in eto1-4 was suppressed, which suggests that the exemplary compounds disrupted the ethylene response (FIG. 1C). The second assay determined the ethylene level in the presence of the exemplary chemical compounds. Results in FIG. 1D show that the excessive level of ethylene in the eto1-4 mutant was reduced to that of the wild type (WT=Col) by the exemplary invention compounds, which indicates that the ethylene biosynthesis was inhibited. Our results demonstrate that the phenotype-based strategy for chemical screening successfully identified small molecules suppressing the ethylene response, most likely by inhibiting ethylene biosynthesis in *Arabidopsis*.

Example 2

Figure 2:
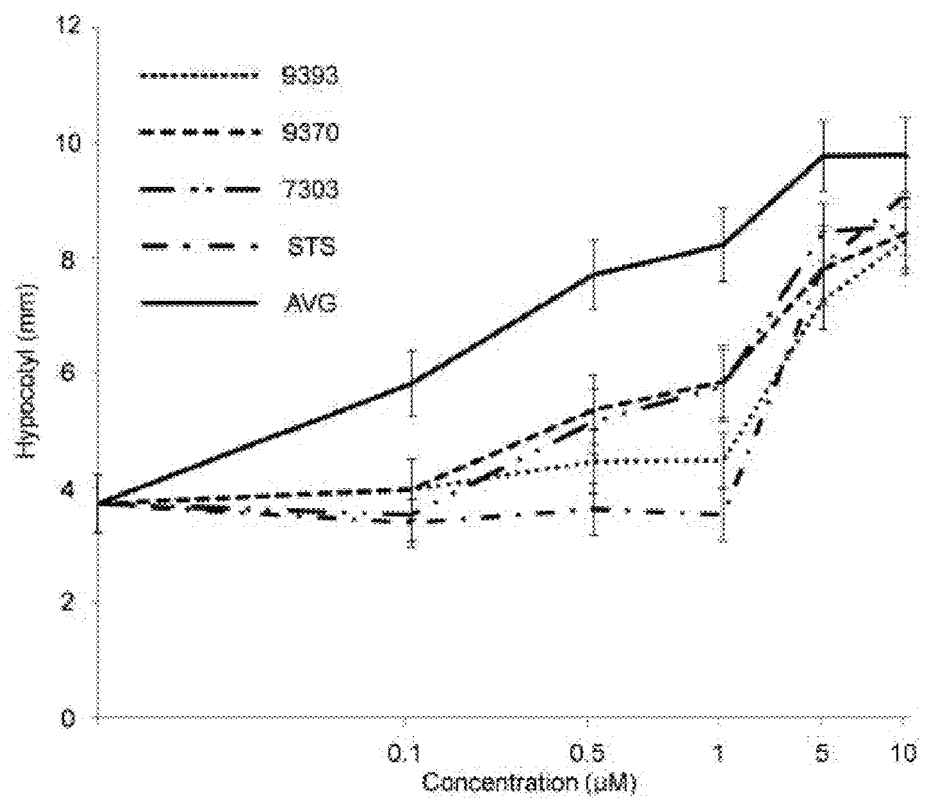
FIG. 2 shows that the screened exemplary invention compounds suppress the hypocotyl phenotype of eto1-4 by a dose-dependent manner. Seeds of eto1-4 were germinated in the dark for 3 days with different concentrations of exemplary invention compounds, STS and AVG. Data are the means of hypocotyl length of etiolated seedlings (n>30) measured by NIH Image J software. Error bars indicate SE.

Determining Whether the Exemplary Invention Compounds have Different Effectiveness in Suppressing the Ethylene Response To determine whether the exemplary invention compounds (e.g. compounds 9393, 9370 and 7303) have different effectiveness in suppressing the ethylene response, the hypocotyl length of etiolated eto1-4 seedlings as a quantitative assay of ethylene response was measured. Shortened hypocotyls in etiolated seedlings is one of the triple response phenotypes (Guzman, et al. (1990) *Plant Cell* 2, 513-523; Wang, et al. (2004) *Nature* 428, 945-950). Two chemical compounds negating ethylene response, AVG and STS, were included as a control for comparison. Both AVG and STS showed effective suppression of the ethylene response, as reflected by elongated hypocotyls in etiolated eto1-4 seedlings (FIG. 2). AVG promoted a visible hypocotyl elongation at as low as 0.1 µM and reached maximal effect at 5 µM. However, STS became effective only at concentrations higher than 1 µM. Compound 9393 resembled STS by showing a visible effect only at concentrations higher than 1 µM. However, both 9370 and 7303 began to suppress the ethylene response in hypocotyls at 0.1 µM and reached a nearly saturated effect at 5 µM, similar to that of AVG. Thus, the exemplary invention compounds suppressed the hypocotyl phenotype of etiolated eto1-4, which resembled AVG or STS at comparable concentrations.

Example 3

Structure and Function Analysis of the Exemplary Invention Compounds and Structural Analogs Seventy four chemical compounds were identified with differential degrees of suppression on eto1-4 phenotype from screening the DIVERSet library (FIG. 1A). Among these compounds, 2 of the effective compounds, compounds 9393 and 9370, contain a quinazolinone backbone (Table 1). A third exemplary compound, 7303, was subsequently identified by structural similarity and was the most effective (Table 1 and FIG. 3). Because the compounds 9379, 9393, and 7303 share an identical skeleton structure with different moieties at the side chains, a structure and functional analysis of compounds with a quinazolinone backbone was performed. From additional DIVERSet collections, 29 structurally analogous small molecules as exemplary invention compounds were selected based on similarity at 85% to compounds 9393 or 9370. Among the 29 compounds, 14 resulted in elongated hypocotyls in etiolated eto1-4 seedlings relatively greater than that in the control (DMSO only) (FIG. 3A). Seven compounds, including the exemplary compounds 9393, 9370, and 7303, have the antagonizing ethylene response to elongate hypocotyls ranged from 28% to 77% of that with AVG treatment (defined as 100%). To determine whether the ethylene level is the key factor in regulating the hypocotyl length in etiolated eto1-4 seedlings, ethylene emanation was quantitatively analyzed in the presence of exemplary chemical compounds by gas chromatography. Fourteen exemplary invention compounds were selected to show differential degrees in suppressing ethylene response in FIG. 3A for ethylene measurement. All of the exemplary 14 compounds were able to reduce ethylene levels in etiolated eto1-4 seedlings at 10 µM (FIG. 3B). Nine of the exemplary 14 compounds were able to suppress ethylene levels greater than 60% of that in etiolated eto1-4 by comparison with the AVG treatment (defined as 100%). Results of quantification of hypocotyl length and ethylene level are in good agreement in that the most effective compounds in both assays including the same group of compounds 9028, 2305, 9393, 9370, 8107, 2616 and 7303 (FIG. 3).

Figures 3A, 3B:
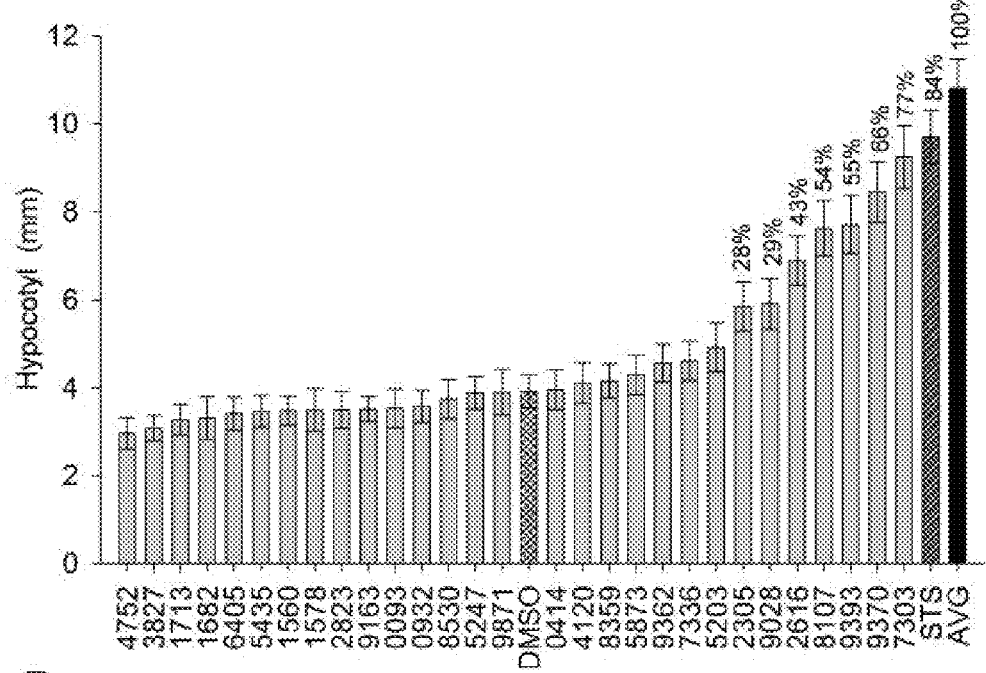
FIGS. 3A and 3B provide results of structural and functional analysis of analogues of the exemplary invention compounds. Quantitation of (3A) hypocotyl length and (3B) ethylene levels of etiolated eto1-4 seedlings in the presence of chemical compounds at 10 µM. Seedlings were germinated in the dark for 3 days before measurement of hypocotyl length (n>40) or quantitation of ethylene (n>30 each GC vials) from at least 3 replicates. The 14 exemplary invention compounds used in FIG. 3B were selected based on the results as in FIG. 3A. Data represent the means±SE and the experiments were repeated twice with similar results. DMSO was used as control. 100% of suppression was assigned to AVG for comparison among the compounds. Full chemical IDs are listed in Table 1.

Based on the side chains at the C7 position of the quinazolinone skeleton, the exemplary chemical structures of 29 compounds analyzed in FIG. 3A are classified into 2 groups (Table 1). The compounds in type I contain aromatic moieties such as phenyl group at position C7, whereas type II compounds have alkyl groups such as methyl at the same position. Four of the 7 most-effective small molecules belong to type I (compounds 7303, 9370, 8107 and 2616), and the remaining 3 compounds are type II (compounds 9393, 9028 and 2305).

Example 4

Figures 4A, 4B, 4C, 4D:
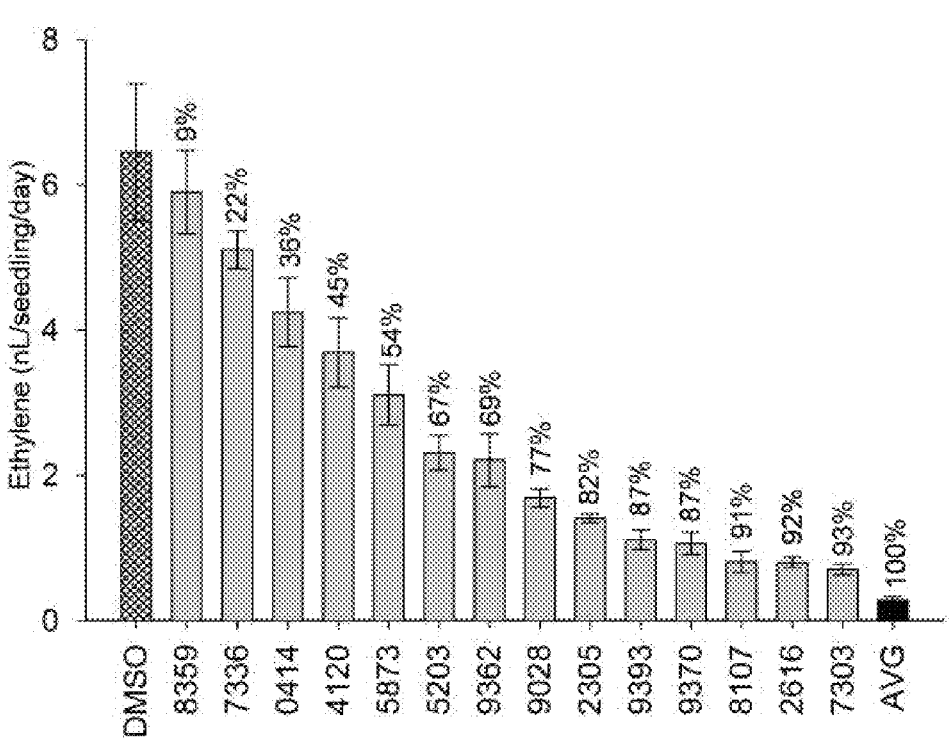
FIG. 4A-4D show that selected exemplary invention compounds specifically suppress the triple response phenotype in eto1-4. Seeds of (FIG. 4A) wild type (WT+ACC at 10 µM), (FIG. 4B) eto1-4, (FIG. 4C) EIN3OX, and (FIG. 4D) ctr1-1 were germinated with exemplary invention compounds (bars 2-4; 10 µM) or DMSO (1; control). Wild type without any chemical treatment is indicated by black bar. Hypocotyl length of etiolated seedlings was quantified and values are means±SE (n>40). A schematic representation of a simplified ethylene pathway is indicated.
Figures 4A, 4B, 4C, 4D, 4E:
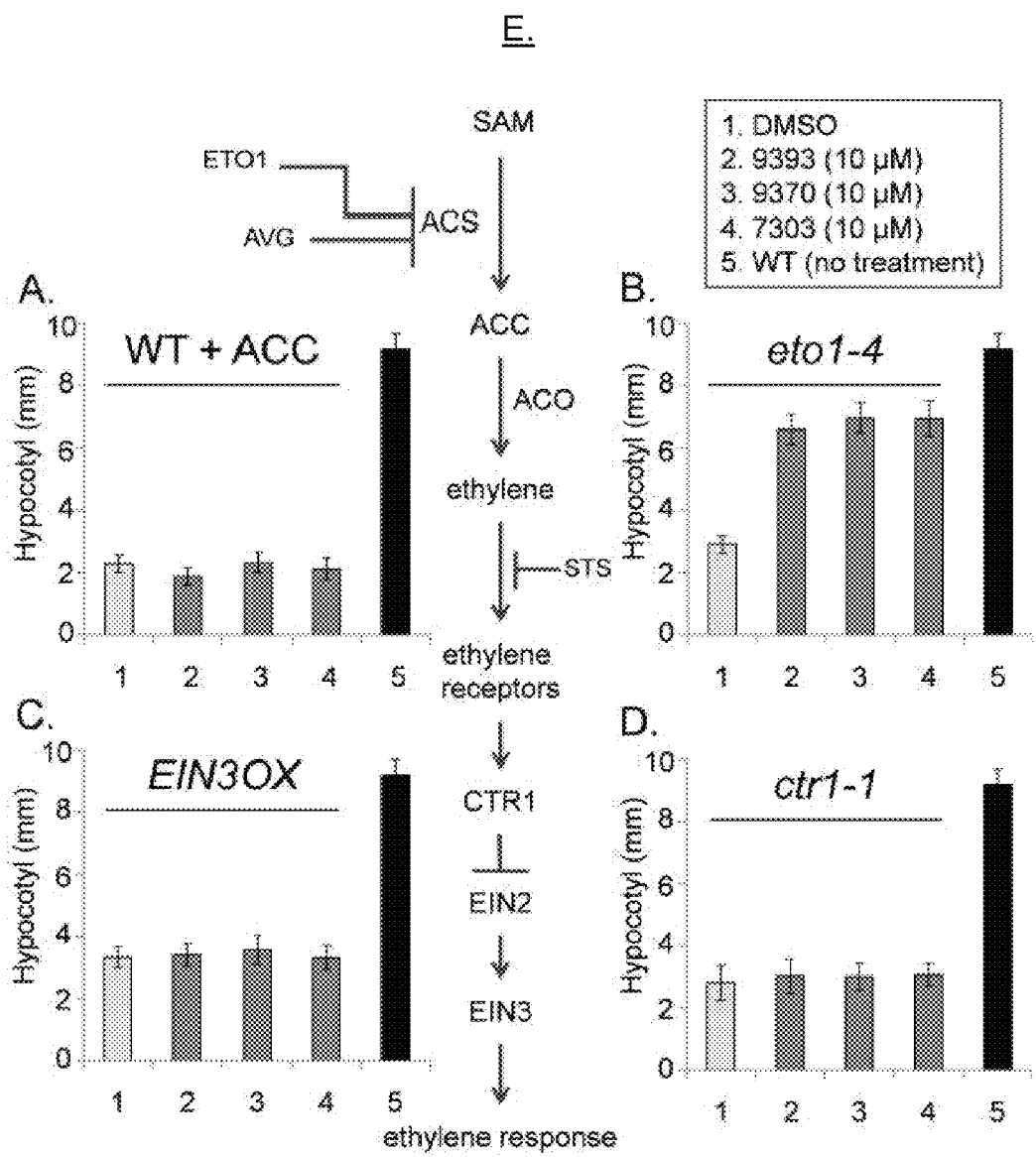

Exploring which Step in the Ethylene Biosynthetic, Pathway is Inhibited by the Exemplary Invention Compounds and Whether the Compounds Affect the Signaling Relay Downstream of Ethylene Receptors It was demonstrated that the exemplary invention compounds reduced ethylene emanation in etiolated eto1-4 seedlings. However, it was not known which step in the ethylene biosynthetic pathway is inhibited and whether the compounds affect the signaling relay downstream of ethylene receptors. To clarify this issue, a quantitative assay of hypocotyl length was used to analyze the effect of exemplary invention compounds in etiolated *Arabidopsis* seedlings. Two ethylene mutants (eto1-4 and ctr1-1) and a transgenic *Arabidopsis* overexpressing EIN3 by the CaMV 35S promoter (35S::EIN3 or EIN3OX) (Chao, et al. (1997) *Cell* 89, 1133-1144) exhibiting a constitutive triple response phenotype were used for analysis. The eto1-4 and ctr1-1 mutants are representative mutants defective in the biosynthetic and signaling pathways, respectively, of ethylene and show a constitutive triple response phenotype. EIN3 and EIN3-like (EIL) proteins are transcription factors responding to ethylene to activate the expression of primary response genes in the nucleus (Chao, et al. (1997) *Cell* 89, 1133-1144). ACC is the immediate precursor of ethylene and is routinely used to induce the triple response in etiolated seedlings. In the absence of exemplary invention compounds, the etiolated seedlings of WT treated with ACC, eto1-4, ctr1-1 and EIN3OX showed a typical triple response, and the length of hypocotyls was measured for quantitative analysis (FIG. 4). The shortened hypocotyl in etiolated wild-type seedlings induced by ACC remained on treatment with the exemplary invention compounds, which suggests that the ACC oxidase and ethylene receptors were not likely the targets and were thus not affected (FIG. 4A). However, the hypocotyls of only etiolated eto1-4 but not ctr1-1 or EIN3OX were elongated in the presence of the exemplary invention compounds, which indicates that the exemplary invention compounds suppressed the constitutive triple response only in eto1-4 but not the signaling pathway downstream of ethylene receptors (FIG. 4B-D). The same results was found using increased concentrations of the exemplary invention compounds up to 50 µM (data not shown). Therefore, the data strongly implies that the exemplary invention compounds are involved in inhibition in the conversion of SAM to ACC catalyzed by ACC synthase.

Example 5

Determining Whether the Exemplary Compounds are Inhibitors of ACC Synthase

The exemplary invention compounds did not suppress the triple response phenotype induced by ACC in etiolated WT seedlings, which suggests that the formation of ethylene from ACC was not affected. Therefore, ACC oxidase as the primary target of exemplary the exemplary invention compounds can be excluded. To determine whether the exemplary invention compounds are inhibitors of ACC synthase, the following assays were used. First, the hypocotyl length and ethylene level in the dominant eto2-1 mutant were analyzed, which bears a missense mutation at the 3' terminus of ACS5 to generate a mutated yet functional protein, $ACS5^{eto2-1}$. $ACS5^{eto2-1}$ results in a constitutive triple response in etiolated seedlings because of producing 10- to 20-fold higher ethylene levels as compared with the WT because $ACS5^{eto2-1}$ no longer interacts with ETO1 and therefore escapes from the negative regulation by ETO1 and the subsequent ubiquitin-proteasome mediated protein degradation (Chae, et al. (2003) *Plant Cell* 15, 545-559; Wang, et al. (2004) *Nature* 428, 945-950). Second, the effect of exemplary invention compounds on the enzymatic activity of recombinant *Arabidopsis* ACS5 protein by an in vitro ACS activity assay was analyzed (Chae, et al. (2003) *Plant Cell* 15, 545-559; Savaldi-Goldstein, et al. (2008) *Proc Natl Acad Sci USA* 105, 15190-15195).

Figure 5:
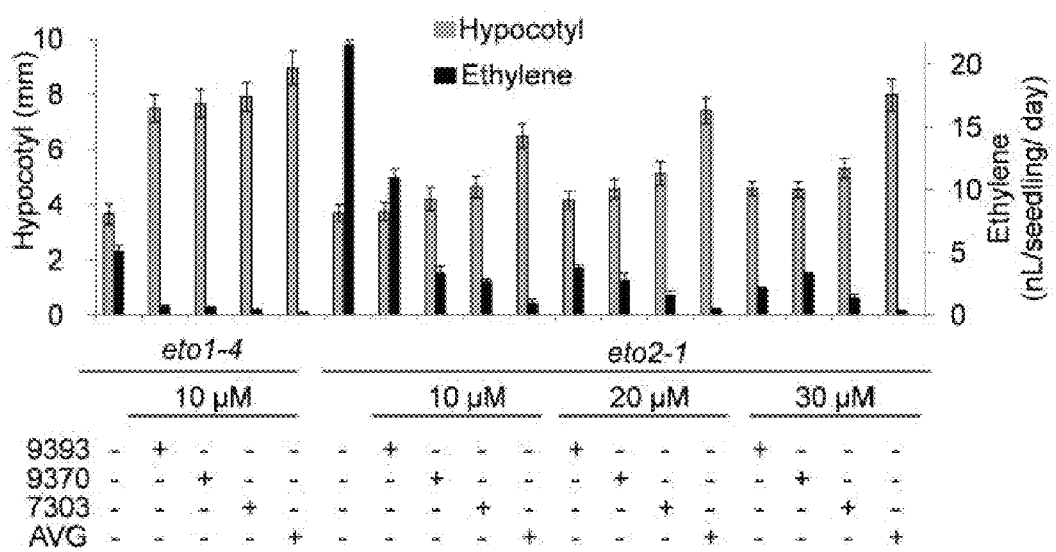
FIG. 5 shows that the selected exemplary invention compounds effect phenotypical suppression of hypocotyls and ethylene levels in two eto mutants. Seeds of eto1-4 and eto2-1 were germinated in the dark in the absence (−) or presence (+) of different concentrations (10, 20 or 30 µM) of exemplary invention compounds and AVG. The length of hypocotyls and ethylene levels were quantified in 3-day-old etiolated seedlings. Data represent means±SE (n>40), and the experiments were repeated 3 times with similar results.

An elongated hypocotyl in the etiolated seedlings of eto mutants reflects the reduced ethylene level in the etiolated seedlings. The length of hypocotyl in etiolated eto1-4 seedlings was increased from an average of 3.8 mm (no treatment) to 72-8 mm in the presence of 10 µM of exemplary compounds and to nearly 9 mm by the same concentration of AVG (FIG. 5). Consistent with the hypocotyl phenotype, the ethylene level in eto1-4 was reduced by the exemplary invention compounds and AVG at 10 µM to a similar extent. It was assessed whether the exemplary invention compounds affected the same phenotype and ethylene level in eto2-1, with nearly fivefold higher ethylene levels than that of eto1-4. The reduced ethylene level and concomitant hypocotyl elongation in etiolated eto2-1 seedlings were observed in the presence of different concentrations of exemplary invention compounds and AVG (FIG. 5). By increasing the concentration from 10 to 30 µM, the exemplary invention compounds resulted in a concentration-dependent reduction of ethylene levels in eto2-1 mutant, which suggests that the hyperactive $ACS5^{eto2-1}$ was inhibited by the compounds. These results imply that the exemplary invention compounds may indeed function as inhibitors of ACS enzyme.

Figures 6A, 6B:
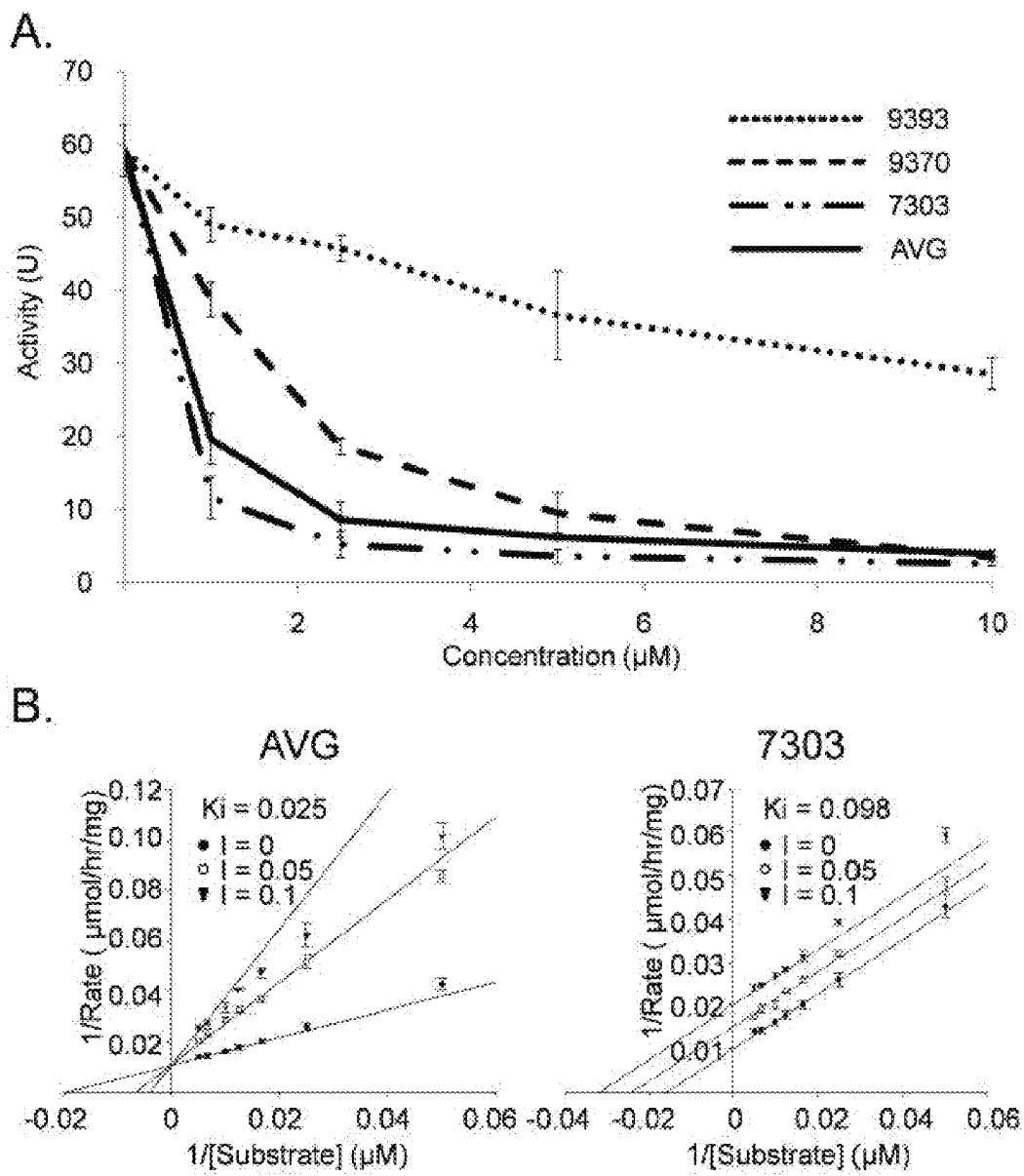
FIGS. 6A and 6B demonstrate that the selected invention compounds are novel inhibitors of ACC synthase.

To further test this possibility, recombinant *Arabidopsis* ACS5 protein from bacterial cells was purified for an in vitro enzyme activity assay. The constituents in the in vitro ACS activity assay include the substrate SAM, co-factor PLP, and a purified ACS5 enzyme. ACC is converted from SAM by ACS and oxidized to ethylene by a chemical reaction for subsequent analysis of ethylene levels by gas chromatography (Lizada, et al. (1979) *Anal Biochem* 100, 140-145). The quantity of ACC converted to ethylene by recombinant ACS5 is the readout of ACS activity. Compounds 9370 and 7303 displayed an apparent inhibition in ACS5 enzyme activity, with estimated half maximal inhibitory concentration ($IC_{50}$) at 1.4 and 0.5 µM, respectively (FIG. 6A). Although compound 9393 showed a comparable effect in suppressing the ethylene level and hypocotyl phenotype in eto1-4 (FIGS. 1B and 1D), it was less effective in the in vitro activity assay, with an estimated $IC_{50}$ at 3.2 µM. However, AVG gave an $IC_{50}$ at approximately 0.7 µM, which is nearly the same as that of compound 7303 (FIG. 6A), which indicates that 7303 is as effective as AVG by the in vitro activity assay. Results from this assay provide direct evidence that exemplary invention compounds are inhibitors of ACS enzyme.

AVG and its analogs are competitive inhibitors of ACC synthase (Boller, et al. (1979) *Planta* 145, 293-303). Because the exemplary invention compounds and AVG have distinct chemical structures (Table 1), they may use different mechanisms to inhibit ACC synthase. To clarify this issue, compound 7303 was selected as a representative of the exemplary invention compounds for enzyme kinetic assay to determine the inhibitory mechanism. FIG. 6B shows the Lineweaver-Burk plot of recombinant ACS5 treated with AVG or compound 7303 at 0.05 and 0.1 µM. Inhibition patterns from these experiments indicate that AVG behaves as a competitive inhibitor and compound 7303 an uncompetitive inhibitor. The kinetic parameters (Km and Vmax) for AVG (Km=51.0 µM; Vmax=92.2 µmol $h^{-1}$ $mg^{-1}$) and 7303 (Km=49.6 µM; Vmax=92.4 µmol $h^{-1}$ $mg^{-1}$) did not significantly differ. However, the calculated inhibition constant (Ki) obtained from enzyme kinetic assays was 25.6±2.1 and 98.4±6.7 nM for AVG and compound 7303, respectively, which indicates that AVG is a more effective inhibitor of ACS5 than compound 7303. Data from the enzyme kinetic assay support that the exemplary invention compounds are novel inhibitors of ACC synthase different from AVG and show uncompetitive inhibition in ACS activity.

Global Analysis of Gene Expression Profiles by the Exemplary Invention Compounds.

It was showed that the exemplary invention compounds had different potencies: for example, compound 9393 was the least effective, with 2 to 4-fold higher $IC_{50}$ than compounds 9370 and 7303 (FIG. 6A). However, these compounds did not differ in suppression of the triple response and ethylene emanation of etiolated eto1-4 seedlings at 10 µM (FIGS. 4 and 5). The exemplary invention compounds may be metabolized to an identical active product after entering the plant cells, thus modulating the same biological process and leading to a similar phenotype. Alternatively, the concentration may be already saturated for phenotype analyses, regardless of the potential issues of permeability and structural modifications in the cells. To address this issue at the gene expression level, total RNA was extracted from 3-day-old etiolated seedlings of WT and eto1-4 in the absence and presence of the exemplary invention compounds or AVG for transcriptome analysis with *Arabidopsis* ATH1 GeneChip for microarray experiments.

Figures 7A, 7B, 7C:
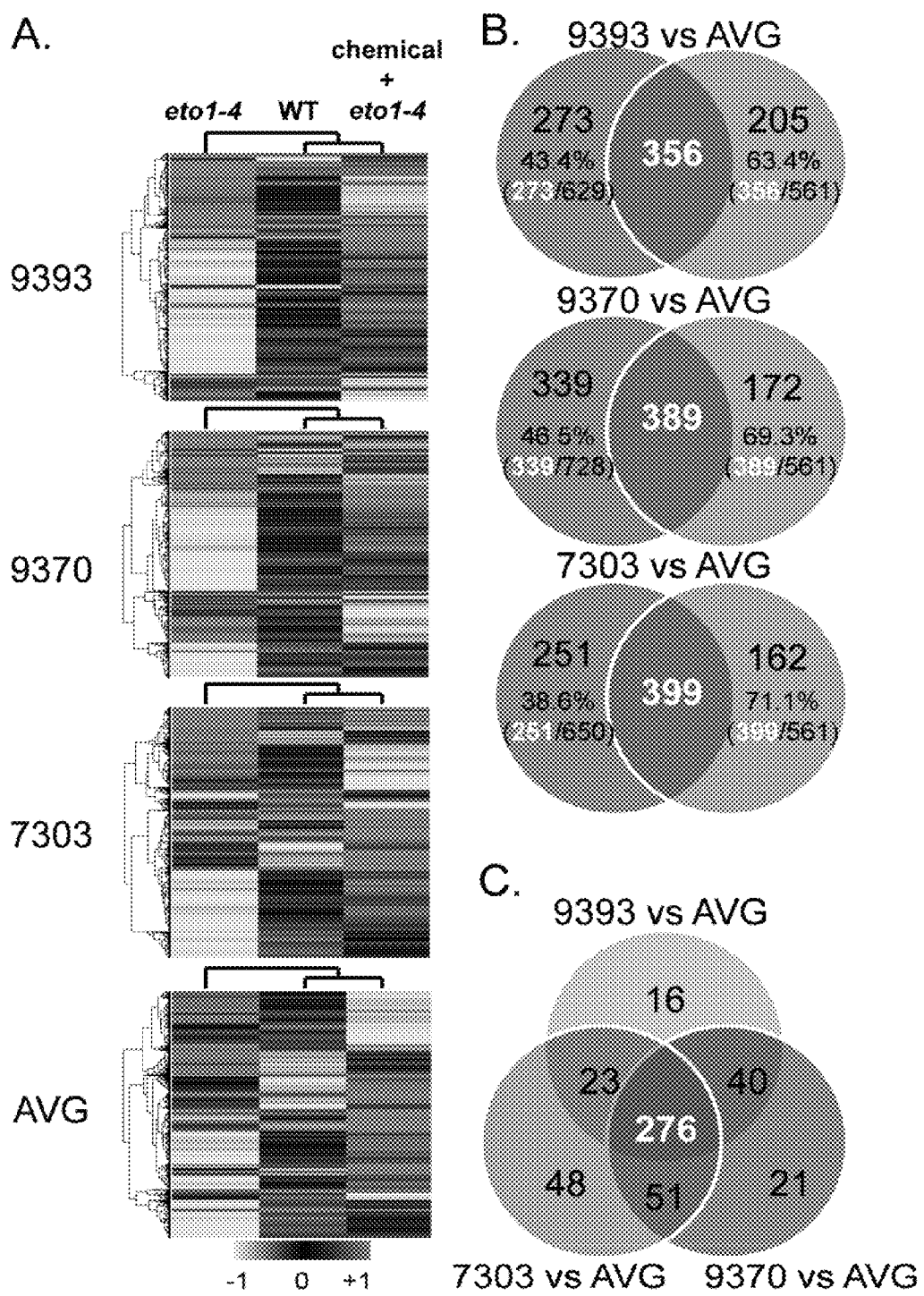
FIG. 7A-7C provide global analysis of gene expression profiles in eto1-4 in the presence of the exemplary invention compounds and AVG.

The filtered and normalized expression data set from 22810 probes on the ATH1 Genechip was used for hierarchical clustering of gene expression profiles for comparison between AVG and the exemplary invention compounds in eto1-4. It was identified that 1,446 genes show at least 1.5-fold difference in expression between the WT and eto1-4 and used them as the master gene pool for clustering analysis (FIG. 7A). Of the 1446 genes, 629 (43.5%), 728 (50.3%), 650 (45.0%) and 561 (38.8%) are regulated by compounds 9393, 9370, 7303 and AVG, respectively; expression levels reverted close to that in the WT by chemical treatments in eto1-4. These genes likely contribute to the etiolated phenotype of eto1-4 by responding to elevated endogenous ethylene. To determine whether the exemplary compounds have specific r overlapping functions with AVG to suppress the eto1-4 phenotype, genes that are regulated by individual exemplary invention compounds and AVG for Venn diagram analysis were clustered (FIG. 7B). More than 63% of genes (356/561 for compound 9393; 389/561 for compound 9370; 399/561 for compound 7303; FIG. 7B) with expression associated with AVG were co-regulated by the exemplary invention compounds, which indicates an overlap function in suppression of the ethylene phenotype in eto1-4. However, approximately 40% of genes (273/629 for compound 9393; 339/728 for compound 9370; 251/650 for compound 7303; FIG. 7B) with expression not related to AVG treatment were specifically regulated by individual exemplary invention compounds, which suggests that the exemplary invention compounds may also affect AVG-independent biological processes. Next genes co-regulated by all of the exemplary invention compounds and AVG were examined by performing a clustering analysis using the co-regulated genes identified in FIG. 7B: 356 (compound 9393 vs AVG), 389 (compound 9370 vs AVG) and 399 genes (compound 7303 vs AVG). It was uncovered that 276 genes were co-regulated by all of the exemplary invention compounds and AVG (FIG. 7C and Table 2). On the basis of GO descriptions generated by Gene Spring GX and TAIR database, the 276 genes were divided into subgroups related to their biological functions (Table 2). Several genes are involved in biosynthesis and response of phytohormones, including auxin, ethylene, abscisic acid and gibberellic acid, which suggests that a cross-talk among phytohormones contributes to the triple response phenotype in eto1-4. The results also showed different types of transcription factors, such as those in AP2/EREBP, bHLH, bZIP, zinc finger (C2H2- and C3HC4-type), myb and WRKY gene families. In addition, stress- and pathogenesis-related genes were among the co-regulated genes, possibly because ethylene is involved in both biotic and abiotic stresses.

Genes (1446 non-redundant loci) were selected by 1.5-fold differential expression between eto1-4 and WT as the master pool for analysis. These genes were used for comparison between chemical treatments by AVG and the exemplary invention compounds. The finalized 276 genes that are co-regulated by AVG and all of the exemplary invention compounds are shown. Locus ID also present in Nemhauser et al. (Nemhauser, et al. (2006) *Cell* 126, 467-475). Numbers are showed in bold.

TABLE 2

Expression fold change of genes regulated by AVG and exemplary compounds.

| Locus ID# | Signal Fold Change* | | | | | | Functional Description |
|---|---|---|---|---|---|---|---|
| | I | II | III | IV | V | | |
| | | | | Metabolism | | | |
| AT1G31710 | 4.71 | 3.17 | 4.67 | 5.43 | 6.59 | amine metabolic process | copper amine oxidase |
| AT2G26740 | 0.36 | 0.29 | 0.23 | 0.26 | 0.44 | aromatic compound metabolic process | epoxide hydrolase |
| AT5G41900 | 3.34 | 2.67 | 3.08 | 4.02 | 2.23 | aromatic compound metabolic process | hydrolase |
| AT5G59540 | 0.43 | 0.44 | 0.40 | 0.34 | 0.33 | ATP synthesis coupled proton transport | oxidoreductase |
| AT1G64200 | 1.88 | 2.10 | 2.41 | 2.73 | 2.58 | ATP synthesis coupled proton transport | V-ATPase E subunit |
| AT2G35710 | 1.98 | 2.39 | 2.23 | 2.25 | 1.87 | biosynthetic process | glycogenin glucosyltransferase |
| AT1G08990 | 2.12 | 1.61 | 2.25 | 2.60 | 2.90 | biosynthetic process | glycogenin glucosyltransferase |
| AT3G04010 | 1.99 | 2.09 | 1.98 | 3.80 | 2.01 | carbohydrate metabolic process | glycosyl hydrolase |
| AT3G44990 | 0.40 | 0.28 | 0.22 | 0.21 | 0.23 | carbohydrate metabolic process | endo-xyloglucan transferase |
| AT4G18340 | 1.87 | 2.57 | 2.70 | 3.43 | 3.40 | carbohydrate metabolic process | glycosyl hydrolase |
| AT5G66460 | 0.59 | 0.51 | 0.42 | 0.52 | 0.42 | carbohydrate metabolic process | (1-4)-beta-mannan endohydrolase |
| AT5G08370 | 4.58 | 2.77 | 4.06 | 3.99 | 3.78 | carbohydrate metabolic process | alpha-galactosidase |
| AT5G13870 | 0.30 | 0.27 | 0.11 | 0.19 | 0.17 | carbohydrate metabolic process | endo-xyloglucan transferase |
| AT1G10760 | 0.86 | 0.46 | 0.33 | 0.43 | 0.45 | carbohydrate metabolic process | starch excess protein (SEX1) |
| AT1G15380 | 1.68 | 1.96 | 2.66 | 2.99 | 3.79 | carbohydrate metabolic process | lactoylglutathione lyase |
| AT5G15530 | 0.39 | 0.54 | 0.38 | 0.43 | 0.42 | fatty acid biosynthetic process | biotin carboxyl carrier protein 2 |
| AT3G30775 | 2.31 | 2.13 | 3.13 | 4.43 | 4.30 | glutamate biosynthetic process | proline oxidase, mitochondrial |
| AT4G39210 | 0.55 | 0.44 | 0.28 | 0.34 | 0.29 | glycogen biosynthetic process | ADP-glucose pyrophosphorylase |
| AT4G39800 | 2.68 | 2.16 | 2.08 | 2.69 | 1.98 | inositol biosynthetic process | inositol-3-phosphate synthase isozyme 1 |
| AT3G10340 | 1.85 | 2.17 | 1.94 | 2.63 | 3.63 | L-phenylalanine catabolic process | phenylalanine ammonia-lyase |
| AT3G29250 | 5.14 | 4.05 | 5.52 | 20.57 | 11.80 | metabolic process | short-chain dehydrogenase |
| AT4G03140 | 0.40 | 0.41 | 0.38 | 0.23 | 0.22 | metabolic process | short-chain dehydrogenase |
| AT3G59710 | 0.45 | 0.39 | 0.38 | 0.48 | 0.29 | metabolic process | short-chain dehydrogenase |
| AT3G46700 | 2.32 | 3.09 | 5.15 | 7.33 | 5.14 | metabolic process | UDP-glucosyl transferase |
| AT4G15550 | 0.22 | 0.36 | 0.28 | 0.39 | 0.53 | metabolic process | UDP-glucose:indole-3-acetate beta-D-glucosyltransferase |
| AT5G02540 | 0.10 | 0.17 | 0.12 | 0.33 | 0.90 | metabolic process | short-chain dehydrogenase |
| AT5G14780 | 0.53 | 0.44 | 0.35 | 0.41 | 0.49 | metabolic process | formate dehydrogenase |
| AT1G49660 | 0.35 | 0.38 | 0.34 | 0.47 | 0.42 | metabolic process | expressed protein |
| AT1G80380 | 1.67 | 2.17 | 2.14 | 2.20 | 2.54 | photorespiration | phosphoribulokinase |
| AT3G12500 | 2.77 | 1.85 | 1.91 | 3.58 | 3.45 | polysaccharide catabolic process | basic endoexemplary inase |
| AT5G18670 | 0.45 | 0.50 | 0.40 | 0.63 | 0.49 | polysaccharide catabolic process | beta-amylase |
| AT1G06720 | 1.01 | 1.15 | 1.28 | 1.26 | 1.26 | ribosome biogenesis and assembly | expressed protein |
| AT3G52180 | 0.76 | 0.32 | 0.25 | 0.22 | 0.29 | starch metabolic process | protein tyrosine phosphatase |
| AT2G47510 | 0.65 | 0.53 | 0.43 | 0.48 | 0.57 | tricarboxylic acid cycle | fumarate hydratase |
| | | | | Phytohormone | | | |
| AT1G78240 | 0.57 | 0.49 | 0.47 | 0.54 | 0.52 | response to cytokinin stimulus | dehydration-responsive protein |
| AT2G19590 | 0.36 | 0.29 | 0.28 | 0.28 | 0.19 | ethylene biosynthetic process | ACC oxidase |
| AT4G34760 | 0.07 | 0.20 | 0.15 | 0.22 | 0.17 | response to auxin stimulus | auxin-responsive protein |
| AT4G12410 | 2.05 | 2.76 | 2.89 | 3.30 | 2.72 | response to auxin stimulus | auxin-responsive protein |
| AT2G16580 | 2.78 | 2.33 | 2.83 | 2.29 | 1.95 | response to auxin stimulus | auxin-responsive protein |
| AT3G50660 | 3.70 | 4.32 | 4.00 | 4.40 | 3.79 | response to brassinosteroid stimulus | steroid 22-alpha-hydroxylase |
| AT2G26070 | 0.20 | 0.32 | 0.28 | 0.28 | 0.47 | response to ethylene stimulus | expressed protein |
| AT5G14920 | 0.27 | 0.35 | 0.31 | 0.33 | 0.45 | response to gibberellin stimulus | gibberellin-regulated protein |
| AT2G24150 | 2.03 | 2.23 | 2.23 | 1.90 | 1.79 | response to hormone stimulus | expressed protein |
| | | | | Transcription | | | |
| AT1G66230 | 2.01 | 3.04 | 2.70 | 3.14 | 3.00 | regulation of transcription | myb transcription factor (MYB20) |
| AT5G39860 | 2.43 | 2.39 | 3.46 | 4.44 | 5.57 | regulation of transcription | bHLH protein |
| AT3G25710 | 2.93 | 2.27 | 2.47 | 2.51 | 2.75 | regulation of transcription | bHLH protein |
| AT2G25900 | 0.30 | 1.27 | 1.48 | 1.73 | 2.32 | regulation of transcription | zinc finger (CCCH-type) protein |
| AT1G67030 | 4.38 | 6.01 | 7.63 | 10.77 | 7.71 | regulation of transcription | zinc finger (C2H2 type) protein |
| AT1G68520 | 2.45 | 2.45 | 2.74 | 1.15 | 1.47 | regulation of transcription | zinc finger (B-box type) protein |
| AT5G25160 | 1.99 | 2.60 | 3.03 | 2.70 | 2.49 | regulation of transcription | zinc finger (C2H2 type) protein |
| AT4G00730 | 0.59 | 0.55 | 0.54 | 0.54 | 0.48 | regulation of transcription | anthocyaninless2 |
| AT2G02820 | 3.94 | 3.34 | 4.00 | 4.90 | 4.51 | regulation of transcription | myb transcription factor (MYB88) |
| AT2G21880 | 3.43 | 3.83 | 3.99 | 4.62 | 3.70 | regulation of transcription | Ras-related GTP-binding protein |
| AT1G22740 | 1.66 | 2.34 | 2.62 | 3.52 | 3.62 | regulation of transcription | Ras-related protein (RAB7) |

TABLE 2-continued

Expression fold change of genes regulated by AVG and exemplary compounds.

| | | | | | | |
|---|---|---|---|---|---|---|
| AT1G71030 | 2.29 | 4.86 | 5.41 | 8.09 | 5.81 regulation of transcription | myb transcription factor (MYB2) |
| AT5G15830 | 2.65 | 3.94 | 4.18 | 4.29 | 4.09 regulation of transcription | bZIP transcription factor protein |
| AT3G25730 | 0.15 | 0.26 | 0.30 | 0.21 | 0.36 transcription | AP2-containing transcription factor |
| AT3G46130 | 2.13 | 2.63 | 2.15 | 2.20 | 2.76 transcription | myb transcription factor (MYB48) |
| AT3G58710 | 2.16 | 2.14 | 2.65 | 2.61 | 2.01 transcription | WRKY transcription factor |
| AT1G09530 | 0.29 | 0.35 | 0.28 | 0.29 | 0.37 transcription | phytochrome interacting factor 3 |
| AT1G52830 | 3.22 | 3.44 | 5.14 | 4.43 | 3.74 transcription | auxin-responsive protein |
| AT1G56010 | 2.05 | 2.29 | 2.65 | 2.97 | 2.43 transcription | transcription activator NAC1 |
| AT1G73830 | 0.09 | 0.28 | 0.37 | 0.20 | 0.40 transcription | bHLH protein |
| AT1G44830 | 0.29 | 0.34 | 0.34 | 0.38 | 0.33 transcription | AP2-containing transcription factor |
| AT1G69570 | 2.62 | 3.88 | 3.22 | 6.31 | 4.24 transcription | Dof-type zinc finger-containing protein |
| AT5G13910 | 0.35 | 0.46 | 0.39 | 0.40 | 0.37 transcription | AP2/EREBP-like transcription factor |
| AT5G25190 | 0.20 | 0.32 | 0.40 | 0.25 | 0.46 transcription | ethylene-responsive element-binding protein |
| | | | | Protein process | | |
| AT1G48480 | 2.91 | 2.65 | 2.68 | 3.43 | 2.83 protein amino acid phosphorylation | leucine-rich repeat trans-membrane protein kinase |
| AT3G27580 | 0.45 | 0.48 | 0.56 | 0.46 | 0.52 protein amino acid phosphorylation | protein kinase |
| AT2G30360 | 1.01 | 1.81 | 2.02 | 3.63 | 3.59 protein amino acid phosphorylation | CBL-interacting protein kinase 11 (CIPK11) |
| AT2G36350 | 0.53 | 0.54 | 0.55 | 0.54 | 0.50 protein amino acid phosphorylation | protein kinase |
| AT3G15890 | 2.25 | 1.98 | 1.86 | 2.14 | 2.09 protein amino acid phosphorylation | protein kinase |
| AT3G14370 | 0.45 | 0.30 | 0.30 | 0.36 | 0.29 protein amino acid phosphorylation | protein kinase |
| AT3G09780 | 0.54 | 0.55 | 0.50 | 0.40 | 0.41 protein amino acid phosphorylation | protein kinase |
| AT4G09570 | 0.51 | 0.36 | 0.35 | 0.34 | 0.35 protein amino acid phosphorylation | calcium-dependent protein kinase |
| AT3G61160 | 2.65 | 3.26 | 3.86 | 5.02 | 4.94 protein amino acid phosphorylation | shaggy-related protein kinase beta/ASK-beta (ASK2) |
| AT1G07560 | 2.77 | 2.23 | 2.24 | 1.99 | 2.97 protein amino acid phosphorylation | leucine-rich repeat protein kinase |
| AT1G08650 | 1.99 | 1.96 | 2.03 | 3.40 | 3.22 protein amino acid phosphorylation | phosphoenolpyruvate carboxylase kinase |
| AT5G63650 | 0.35 | 0.42 | 0.33 | 0.59 | 1.10 protein amino acid phosphorylation | serine/threonine protein kinase |
| AT5G03160 | 2.25 | 1.90 | 2.78 | 2.24 | 2.09 protein folding | DNAJ heat shock N-terminal domain-containing protein |
| AT5G47330 | 2.51 | 2.52 | 3.02 | 2.34 | 2.13 protein modification process | palmitoyl protein thioesterase protein |
| AT5G22860 | 4.39 | 2.63 | 3.54 | 3.07 | 1.96 proteolysis | serine carboxypeptidase S28 protein |
| AT1G73300 | 2.00 | 1.94 | 2.36 | 1.69 | 2.92 proteolysis | serine carboxypeptidase S10 protein |
| AT1G73310 | 3.27 | 2.66 | 2.66 | 4.07 | 3.01 proteolysis | serine carboxypeptidase S10 protein |
| AT1G62290 | 0.43 | 0.32 | 0.27 | 0.38 | 0.41 proteolysis | aspartyl protease protein |
| AT5G08260 | 0.88 | 0.50 | 0.38 | 0.35 | 0.32 proteolysis | serine carboxypeptidase S10 protein |
| AT4G11310 | 6.17 | 8.01 | 9.04 | 17.92 | 23.67 proteolysis | cysteine proteinase |
| AT5G52120 | 3.38 | 5.39 | 7.26 | 11.57 | 12.70 ubiquitin cycle | SKP1 interacting partner 3 protein |
| AT3G23150 | 0.12 | 0.15 | 0.16 | 0.18 | 0.33 two-component signal transduction system (phosphorelay) | ethylene receptor, putative (ETR2) |
| AT5G10720 | 0.44 | 0.48 | 0.32 | 0.36 | 0.34 two-component signal transduction system (phosphorelay) | sensory transduction histidine kinase |
| | | | | Development | | |
| AT3G25980 | 2.48 | 2.35 | 2.23 | 2.49 | 2.57 cell cycle | mitotic spindle checkpoint protein |
| AT4G17220 | 1.91 | 2.49 | 2.35 | 2.48 | 2.25 cytoskeleton organization and biogenesis | expressed protein |
| AT2G35300 | 1.60 | 1.93 | 1.92 | 2.86 | 2.25 embryonic development | late embryogenesis abundant group 1 domain-containing protein |
| AT1G32560 | 3.11 | 1.35 | 1.59 | 1.89 | 2.03 embryonic development | late embryogenesis abundant group 1 domain-containing protein |
| AT1G70210 | 2.74 | 3.05 | 3.28 | 3.72 | 3.86 G1 phase of mitotic cell cycle | cyclin delta-1 |
| AT1G76540 | 2.69 | 2.16 | 2.53 | 2.97 | 2.56 G2/M transition of mitotic cell cycle | cell division control protein |
| AT2G22860 | 1.79 | 2.20 | 2.67 | 2.10 | 3.78 multicellular organismal development | phytosulfokines 2 (PSK2) |

TABLE 2-continued

Expression fold change of genes regulated by AVG and exemplary compounds.

| | | | | | | |
|---|---|---|---|---|---|---|
| AT3G49780 | 3.13 | 4.97 | 7.46 | 9.23 | 9.13 multicellular organismal development | phytosulfokines 3 (PSK3) |
| AT1G27380 | 2.15 | 2.10 | 1.96 | 2.14 | 2.03 pollen tube growth | p21-rho-binding domain-containing protein |

Stress

| | | | | | | |
|---|---|---|---|---|---|---|
| AT2G44130 | 2.32 | 3.36 | 3.39 | 4.62 | 3.49 autophagy | kelch repeat containing F-box protein |
| AT5G20410 | 2.69 | 2.77 | 3.75 | 2.86 | 1.98 response to phosphate starvation | monogalactosyldiacylglycerol synthase |
| AT1G05010 | 0.19 | 0.28 | 0.28 | 0.30 | 0.55 defense response | ACC oxidase |
| AT1G70850 | 8.85 | 7.24 | 9.49 | 22.18 | 24.40 defense response | Bet v I allergen protein |
| AT1G70890 | 5.34 | 5.37 | 5.19 | 5.05 | 5.82 defense response | major latex protein |
| AT2G43535 | 4.12 | 4.42 | 6.13 | 6.32 | 5.08 defense response | trypsin inhibitor |
| AT2G44110 | 0.40 | 0.45 | 0.39 | 0.43 | 0.36 defense response | seven transmembrane MLO protein |
| AT4G11280 | 2.25 | 1.87 | 2.29 | 2.00 | 2.34 defense response | ACC synthase 6 |
| AT3G52920 | 2.00 | 3.09 | 2.82 | 3.88 | 4.19 defense response | expressed protein |
| AT5G65970 | 2.91 | 2.60 | 2.88 | 2.84 | 3.05 defense response | seven transmembrane MLO protein |
| AT5G09980 | 0.51 | 0.35 | 0.38 | 0.28 | 0.38 defense response | expressed protein |
| AT4G11190 | 17.22 | 5.56 | 9.98 | 9.71 | 8.84 defense response | disease resistance-responsive protein |
| AT1G50560 | 2.67 | 1.77 | 2.32 | 2.50 | 2.52 oxidation reduction | cytochrome P450 |
| AT1G72230 | 3.18 | 2.45 | 3.09 | 2.98 | 2.66 oxidation reduction | plastocyanin like protein |
| AT3G20130 | 1.85 | 1.72 | 1.73 | 1.89 | 1.65 oxidation reduction | cytochrome P450 |
| AT2G34500 | 3.53 | 3.82 | 4.05 | 8.32 | 4.80 oxidation reduction | cytochrome P450 |
| AT5G63450 | 5.89 | 6.43 | 8.71 | 16.44 | 10.17 oxidation reduction | cytochrome P450 |
| AT5G25140 | 2.33 | 4.21 | 5.04 | 6.66 | 4.47 oxidation reduction | cytochrome P450 |
| AT3G16450 | 2.32 | 2.09 | 2.54 | 3.13 | 2.47 response to cold | jacalin lectin protein |
| AT3G16470 | 8.78 | 4.09 | 5.60 | 6.91 | 6.63 response to cold | jacalin lectin protein |
| AT2G33380 | 0.47 | 0.26 | 0.21 | 0.22 | 0.28 response to desiccation | calcium-binding RD20 protein |
| AT2G27140 | 2.52 | 2.32 | 2.43 | 2.74 | 3.40 response to heat | heat shock protein |
| AT1G14540 | 0.74 | 0.46 | 0.53 | 0.42 | 0.46 response to oxidative stress | anionic peroxidase |
| AT3G21770 | 2.51 | 1.57 | 2.01 | 1.84 | 2.03 response to oxidative stress | peroxidase 30 |
| AT2G37130 | 2.28 | 1.93 | 2.23 | 2.23 | 1.99 response to oxidative stress | peroxidase 21 |
| AT4G26010 | 0.32 | 0.45 | 0.38 | 0.49 | 0.34 response to oxidative stress | peroxidase |
| AT5G19890 | 0.07 | 0.13 | 0.08 | 0.03 | 0.03 response to oxidative stress | peroxidase |
| AT5G50720 | 2.03 | 2.52 | 2.65 | 2.97 | 3.55 response to stress | ABA-responsive protein (HVA22e) |
| AT5G66400 | 0.53 | 1.09 | 0.81 | 1.10 | 1.47 response to stress | dehydrin (RAB18) |
| AT4G37220 | 5.02 | 7.29 | 6.12 | 15.33 | 16.04 response to stress | stress-responsive protein |
| AT1G05760 | 2.70 | 2.69 | 3.58 | 3.70 | 4.41 response to virus | jacalin lectin protein |
| AT1G73330 | 9.28 | 2.84 | 4.31 | 31.27 | 20.14 response to water deprivation | protease inhibitor |

Transport

| | | | | | | |
|---|---|---|---|---|---|---|
| AT2G40420 | 1.71 | 1.87 | 2.03 | 3.56 | 3.97 amino acid transport | amino acid transporter |
| AT4G12480 | 0.17 | 0.20 | 0.17 | 0.06 | 0.09 lipid transport | lipid transfer protein |
| AT1G62510 | 0.48 | 1.63 | 2.17 | 2.20 | 3.17 lipid transport | lipid transfer protein |
| AT5G46890 | 4.51 | 3.64 | 3.94 | 3.10 | 2.57 lipid transport | lipid transfer protein |
| AT5G48490 | 8.15 | 9.12 | 12.97 | 3.78 | 2.24 lipid transport | lipid transfer protein |
| AT4G35060 | 2.96 | 3.14 | 3.80 | 3.90 | 3.19 metal ion transport | copper chaperone |
| AT1G18880 | 2.07 | 2.00 | 1.93 | 2.51 | 2.12 oligopeptide transport | proton-dependent oligopeptide transport (POT) protein |
| AT1G59740 | 0.31 | 0.46 | 0.39 | 0.32 | 0.27 oligopeptide transport | proton-dependent oligopeptide transport (POT) protein |
| AT3G45710 | 5.68 | 1.98 | 2.40 | 4.30 | 4.10 oligopeptide transport | proton-dependent oligopeptide transport (POT) protein |
| AT1G73220 | 4.34 | 2.95 | 3.97 | 5.76 | 3.23 transport | sugar transporter protein |
| AT2G02850 | 0.30 | 0.27 | 0.23 | 0.15 | 0.13 transport | plantacyanin |
| AT1G73590 | 2.32 | 2.02 | 2.08 | 2.03 | 2.09 transport | auxin efflux carrier protein |
| AT3G22620 | 1.84 | 1.94 | 2.14 | 2.70 | 1.97 transport | lipid transfer protein |
| AT2G29340 | 0.38 | 0.47 | 0.30 | 0.39 | 0.44 transport | short-chain dehydrogenase |
| AT2G39010 | 1.88 | 1.84 | 2.05 | 1.95 | 1.93 transport | aquaporin |
| AT5G47450 | 1.92 | 2.24 | 2.71 | 2.81 | 2.49 transport | major intrinsic protein |
| AT1G32410 | 1.62 | 1.62 | 2.06 | 1.75 | 1.69 transport | vacuolar protein sorting 55 protein |

Other biological functions

| | | | | | | |
|---|---|---|---|---|---|---|
| AT4G23410 | 2.02 | 1.97 | 2.34 | 1.83 | 2.76 aging | senescence-associated protein |
| AT2G47550 | 0.42 | 0.39 | 0.39 | 0.49 | 0.37 cell wall modification | pectinesterase protein |
| AT2G43050 | 2.62 | 2.06 | 2.35 | 3.42 | 2.45 cell wall modification | pectinesterase protein |
| AT2G26440 | 0.60 | 0.36 | 0.38 | 0.27 | 0.29 cell wall modification | pectinesterase protein |
| AT3G43270 | 0.36 | 0.26 | 0.20 | 0.33 | 0.33 cell wall modification | pectinesterase protein |
| AT1G20190 | 0.40 | 0.43 | 0.31 | 0.43 | 0.52 cell wall organization and biogenesis | expansin (EXP11) |
| AT5G56320 | 4.15 | 3.15 | 2.90 | 4.57 | 3.80 cell wall organization and biogenesis | expansin (EXP14) |
| AT5G02260 | 0.16 | 0.16 | 0.10 | 0.23 | 0.33 cell wall organization and biogenesis | expansin (EXP9) |

TABLE 2-continued

Expression fold change of genes regulated by AVG and exemplary compounds.

| | | | | | | | |
|---|---|---|---|---|---|---|---|
| AT3G12030 | 1.65 | 1.73 | 2.17 | 2.06 | 2.47 | DNA repair | expressed protein |
| AT2G01910 | 2.25 | 2.21 | 2.62 | 2.92 | 2.48 | microtubule nucleation | microtubule associated protein (MAP65/ASE1) protein |
| AT5G66310 | 0.57 | 0.48 | 0.45 | 0.48 | 0.36 | microtubule-based movement | kinesin motor protein |
| AT1G76500 | 0.32 | 0.39 | 0.42 | 0.38 | 0.44 | photomorphogenesis | DNA-binding protein |
| AT5G12170 | 0.40 | 0.36 | 0.34 | 0.34 | 0.28 | response to cadmium ion | expressed protein |
| AT1G13430 | 0.45 | 0.38 | 0.28 | 0.34 | 0.17 | response to cytokinin stimulus | sulfotransferase protein |
| AT3G44820 | 2.64 | 2.81 | 2.56 | 2.99 | 2.31 | response to light stimulus | phototropic-responsive NPH3 protein |
| AT4G38690 | 2.27 | 2.55 | 3.04 | 3.39 | 4.44 | signal transduction | 1-phosphatidylinositol |
| AT3G05990 | 2.11 | 2.05 | 2.15 | 2.33 | 2.08 | signal transduction | phosphodiesterase leucine-rich repeat protein |
| AT1G73640 | 2.62 | 1.94 | 2.10 | 2.12 | 1.65 | small GTPase mediated signal transduction | Ras-related GTP-binding protein |
| AT2G29440 | 0.26 | 0.31 | 0.20 | 0.26 | 0.13 | toxin catabolic process | glutathione S-transferase |

Unknown biological function

| | Signal Fold Change* | | | | | | Signal Fold Change* | | | | |
|---|---|---|---|---|---|---|---|---|---|---|---|
| Locus ID# | I | II | III | IV | V | Locus ID# | I | II | III | IV | V |
| AT1G33470 | 1.82 | 2.32 | 2.21 | 2.38 | 2.13 | AT3G17680 | 0.36 | 0.33 | 0.24 | 0.17 | 0.18 |
| AT1G33790 | 0.18 | 0.20 | 0.18 | 0.21 | 0.24 | AT3G23800 | 0.45 | 0.46 | 0.40 | 0.33 | 0.28 |
| AT1G34040 | 3.30 | 1.69 | 2.08 | 2.17 | 2.27 | AT3G24670 | 0.33 | 0.32 | 0.32 | 0.38 | 0.43 |
| AT1G35350 | 3.40 | 3.85 | 4.97 | 4.37 | 3.47 | AT3G28290 | 0.23 | 0.29 | 0.18 | 0.27 | 0.32 |
| AT1G35612 | 1.88 | 3.38 | 3.56 | 3.19 | 3.31 | AT3G47210 | 1.88 | 2.53 | 2.73 | 3.50 | 2.66 |
| AT1G42470 | 2.26 | 4.11 | 4.28 | 4.79 | 4.32 | AT3G47250 | 3.64 | 3.68 | 4.89 | 5.15 | 14.53 |
| AT1G44800 | 2.50 | 1.86 | 1.93 | 2.25 | 2.47 | AT3G51410 | 0.30 | 0.32 | 0.32 | 0.21 | 0.19 |
| AT1G56020 | 0.61 | 0.60 | 0.50 | 0.49 | 0.47 | AT3G51970 | 2.41 | 2.49 | 2.88 | 3.02 | 2.69 |
| AT1G58070 | 1.81 | 2.13 | 2.32 | 2.37 | 2.35 | AT3G53540 | 0.37 | 0.38 | 0.35 | 0.41 | 0.57 |
| AT1G59590 | 2.12 | 2.57 | 3.53 | 3.94 | 3.42 | AT3G56480 | 2.59 | 2.21 | 2.39 | 2.86 | 2.29 |
| AT1G62620 | 1.63 | 2.65 | 2.47 | 3.52 | 2.16 | AT3G59370 | 2.30 | 2.91 | 2.99 | 3.33 | 3.19 |
| AT1G65510 | 1.73 | 2.13 | 2.74 | 4.19 | 4.52 | AT3G59900 | 0.31 | 0.43 | 0.39 | 0.39 | 0.33 |
| AT1G65920 | 0.47 | 0.37 | 0.31 | 0.36 | 0.26 | AT3G60520 | 0.34 | 0.27 | 0.28 | 0.30 | 0.42 |
| AT1G68230 | 2.84 | 2.42 | 2.55 | 2.59 | 3.18 | AT4G01410 | 0.44 | 0.40 | 0.27 | 0.54 | 0.59 |
| AT1G71740 | 1.84 | 2.19 | 2.84 | 3.04 | 2.88 | AT4G08300 | 3.11 | 3.06 | 3.20 | 4.13 | 2.72 |
| AT1G75500 | 3.23 | 3.12 | 3.37 | 3.18 | 2.97 | AT4G10910 | 2.34 | 4.86 | 4.65 | 4.49 | 3.84 |
| AT1G76220 | 2.17 | 3.40 | 3.55 | 4.28 | 3.08 | AT4G12080 | 1.67 | 1.88 | 2.05 | 2.09 | 1.96 |
| AT1G76790 | 5.27 | 2.90 | 3.90 | 3.71 | 2.58 | AT4G13210 | 0.33 | 0.29 | 0.25 | 0.27 | 0.18 |
| AT2G16990 | 2.45 | 2.49 | 2.79 | 3.14 | 3.47 | AT4G15920 | 8.31 | 13.52 | 17.08 | 23.20 | 17.58 |
| AT2G19970 | 2.55 | 2.19 | 3.06 | 3.39 | 4.98 | AT4G25780 | 7.67 | 9.02 | 11.52 | 9.00 | 9.59 |
| AT2G20080 | 2.30 | 4.77 | 3.75 | 5.75 | 5.36 | AT4G28085 | 1.98 | 2.86 | 4.84 | 3.16 | 2.58 |
| AT2G20670 | 1.76 | 2.36 | 2.45 | 4.29 | 4.47 | AT4G31000 | 0.46 | 0.55 | 0.61 | 0.51 | 0.50 |
| AT2G21820 | 0.08 | 1.08 | 0.85 | 1.33 | 1.56 | AT4G32920 | 2.38 | 2.39 | 2.35 | 2.81 | 1.91 |
| AT2G27370 | 2.01 | 1.90 | 2.26 | 2.51 | 2.27 | AT4G34560 | 1.70 | 2.00 | 1.85 | 2.51 | 2.53 |
| AT2G28305 | 2.32 | 2.70 | 3.16 | 2.57 | 3.79 | AT4G35150 | 0.33 | 0.32 | 0.28 | 0.31 | 0.27 |
| AT2G28410 | 2.67 | 2.86 | 2.92 | 2.79 | 2.92 | AT4G36520 | 2.02 | 2.71 | 2.70 | 2.99 | 2.51 |
| AT2G33990 | 2.09 | 2.38 | 2.72 | 2.69 | 2.32 | AT4G39840 | 0.54 | 0.37 | 0.29 | 0.36 | 0.32 |
| AT2G34300 | 0.54 | 0.40 | 0.33 | 0.39 | 0.36 | AT5G01210 | 0.27 | 0.33 | 0.31 | 0.37 | 0.48 |
| AT2G34510 | 2.07 | 2.66 | 2.70 | 2.21 | 2.39 | AT5G01300 | 3.16 | 1.40 | 1.40 | 2.28 | 1.52 |
| AT2G34700 | 2.46 | 1.10 | 1.03 | 0.31 | 0.29 | AT5G04080 | 1.96 | 2.48 | 2.55 | 3.07 | 3.65 |
| AT2G36410 | 1.95 | 2.46 | 2.60 | 3.05 | 2.99 | AT5G05180 | 1.78 | 1.79 | 1.95 | 1.98 | 1.87 |
| AT2G38760 | 2.90 | 2.89 | 4.10 | 5.36 | 3.86 | AT5G06200 | 1.70 | 1.94 | 2.10 | 1.99 | 2.16 |
| AT2G38790 | 2.34 | 1.78 | 1.99 | 3.21 | 3.77 | AT5G08240 | 1.61 | 1.79 | 2.31 | 2.56 | 3.14 |
| AT2G39310 | 2.34 | 1.97 | 2.73 | 3.40 | 2.76 | AT5G11540 | 4.44 | 5.32 | 5.68 | 6.69 | 5.10 |
| AT2G39980 | 0.05 | 0.14 | 0.14 | 0.25 | 0.53 | AT5G15290 | 1.94 | 2.43 | 2.42 | 2.99 | 2.83 |
| AT2G41090 | 0.23 | 0.26 | 0.19 | 0.11 | 0.13 | AT5G18470 | 0.21 | 0.13 | 0.18 | 0.24 | 0.30 |
| AT2G41230 | 0.05 | 0.08 | 0.07 | 0.05 | 0.11 | AT5G18860 | 1.95 | 2.02 | 2.08 | 3.13 | 2.71 |
| AT2G42320 | 0.58 | 0.55 | 0.53 | 0.54 | 0.48 | AT5G18970 | 2.90 | 2.49 | 3.58 | 3.98 | 3.94 |
| AT2G48030 | 2.17 | 2.18 | 2.61 | 2.22 | 1.77 | AT5G19930 | 1.65 | 1.64 | 1.64 | 1.84 | 1.74 |
| AT3G09020 | 2.35 | 2.36 | 3.28 | 3.42 | 2.68 | AT5G22310 | 0.27 | 0.37 | 0.31 | 0.46 | 0.35 |
| AT3G10080 | 2.99 | 2.22 | 2.52 | 2.14 | 2.35 | AT5G23750 | 2.13 | 3.60 | 4.16 | 4.93 | 3.96 |
| AT3G11550 | 2.02 | 2.20 | 2.39 | 2.97 | 2.61 | AT5G24870 | 1.80 | 2.16 | 2.17 | 2.71 | 2.22 |
| AT3G13980 | 3.96 | 6.83 | 6.74 | 6.58 | 5.66 | AT5G34940 | 0.63 | 0.49 | 0.46 | 0.44 | 0.54 |
| AT3G14850 | 0.47 | 0.29 | 0.20 | 0.13 | 0.12 | AT5G37300 | 2.73 | 3.86 | 3.03 | 5.67 | 4.08 |
| AT3G16690 | 2.47 | 3.33 | 3.80 | 4.80 | 3.61 | | | | | | |
| AT5G38930 | 0.36 | 0.33 | 0.24 | 0.16 | 0.18 | AT1G75500 | 3.23 | 3.12 | 3.37 | 3.18 | 2.97 |
| AT5G44410 | 2.20 | 3.37 | 3.27 | 2.89 | 2.57 | AT1G76220 | 2.17 | 3.40 | 3.55 | 4.28 | 3.08 |
| AT5G44580 | 0.22 | 0.22 | 0.21 | 0.14 | 0.13 | AT1G76790 | 5.27 | 2.90 | 3.90 | 3.71 | 2.58 |
| AT5G47240 | 1.12 | 3.96 | 4.32 | 8.92 | 7.89 | AT2G16990 | 2.45 | 2.49 | 2.79 | 3.14 | 3.47 |
| AT5G47950 | 1.93 | 1.93 | 2.55 | 4.37 | 3.47 | AT2G19970 | 2.55 | 2.19 | 3.06 | 3.39 | 4.98 |
| AT5G48900 | 0.60 | 0.55 | 0.48 | 0.58 | 0.53 | AT2G20080 | 2.30 | 4.77 | 3.75 | 5.75 | 5.36 |
| AT5G49900 | 2.44 | 2.24 | 2.96 | 3.82 | 2.96 | AT2G20670 | 1.76 | 2.36 | 2.45 | 4.29 | 4.47 |
| AT5G53190 | 4.11 | 4.35 | 6.92 | 7.32 | 4.49 | AT2G21820 | 0.08 | 1.08 | 0.85 | 1.33 | 1.56 |
| AT5G53830 | 0.29 | 0.40 | 0.39 | 0.30 | 0.38 | AT2G27370 | 2.01 | 1.90 | 2.26 | 2.51 | 2.27 |
| AT5G58660 | 0.26 | 0.34 | 0.27 | 0.40 | 0.56 | AT2G28305 | 2.32 | 2.70 | 3.16 | 2.57 | 3.79 |

TABLE 2-continued

Expression fold change of genes regulated by AVG and exemplary compounds.

| | | | | | | | | | | |
|---|---|---|---|---|---|---|---|---|---|---|
| AT5G66440 | 0.42 | 0.30 | 0.31 | 0.32 | 0.24 | AT2G28410 | 2.67 | 2.86 | 2.92 | 2.79 | 2.92 |
| AT5G66780 | 0.04 | 0.78 | 0.86 | 1.48 | 1.24 | AT2G33990 | 2.09 | 2.38 | 2.72 | 2.69 | 2.32 |
| AT1G03457 | 2.05 | 2.24 | 2.50 | 3.04 | 2.40 | AT2G34300 | 0.54 | 0.40 | 0.33 | 0.39 | 0.36 |
| AT1G03660 | 1.76 | 1.84 | 2.61 | 1.59 | 2.43 | AT2G34510 | 2.07 | 2.66 | 2.70 | 2.21 | 2.39 |
| AT1G07280 | 0.47 | 0.44 | 0.51 | 0.37 | 0.47 | AT2G34700 | 2.46 | 1.10 | 1.03 | 0.31 | 0.29 |
| AT1G17970 | 2.64 | 2.17 | 2.50 | 2.35 | 1.80 | AT2G36410 | 1.95 | 2.46 | 2.60 | 3.05 | 2.99 |
| AT1G23060 | 0.40 | 0.40 | 0.36 | 0.35 | 0.38 | AT2G38760 | 2.90 | 2.89 | 4.10 | 5.36 | 3.86 |
| AT1G26930 | 0.42 | 0.50 | 0.47 | 0.40 | 0.59 | AT2G38790 | 2.34 | 1.78 | 1.99 | 3.21 | 3.77 |
| AT1G29520 | 2.34 | 1.83 | 1.93 | 2.27 | 2.35 | AT2G39310 | 2.34 | 1.97 | 2.73 | 3.40 | 2.76 |
| AT1G30750 | 1.78 | 2.23 | 2.58 | 2.87 | 2.48 | AT2G39980 | 0.05 | 0.14 | 0.14 | 0.25 | 0.53 |
| AT1G33470 | 1.82 | 2.32 | 2.21 | 2.38 | 2.13 | AT2G41090 | 0.23 | 0.26 | 0.19 | 0.11 | 0.13 |
| AT1G33790 | 0.18 | 0.20 | 0.18 | 0.21 | 0.24 | AT2G41230 | 0.05 | 0.08 | 0.07 | 0.05 | 0.11 |
| AT1G34040 | 3.30 | 1.69 | 2.08 | 2.17 | 2.27 | AT2G42320 | 0.58 | 0.55 | 0.53 | 0.54 | 0.48 |
| AT1G35350 | 3.40 | 3.85 | 4.97 | 4.37 | 3.47 | AT2G48030 | 2.17 | 2.18 | 2.61 | 2.22 | 1.77 |
| AT1G35612 | 1.88 | 3.38 | 3.56 | 3.19 | 3.31 | AT3G09020 | 2.35 | 2.36 | 3.28 | 3.42 | 2.68 |
| AT1G42470 | 2.26 | 4.11 | 4.28 | 4.79 | 4.32 | AT3G10080 | 2.99 | 2.22 | 2.52 | 2.14 | 2.35 |
| AT1G44800 | 2.50 | 1.86 | 1.93 | 2.25 | 2.47 | AT3G11550 | 2.02 | 2.20 | 2.39 | 2.97 | 2.61 |
| AT1G56020 | 0.61 | 0.60 | 0.50 | 0.49 | 0.47 | AT3G13980 | 3.96 | 6.83 | 6.74 | 6.58 | 5.66 |
| AT1G58070 | 1.81 | 2.13 | 2.32 | 2.37 | 2.35 | AT3G14850 | 0.47 | 0.29 | 0.20 | 0.13 | 0.12 |
| AT1G59590 | 2.12 | 2.57 | 3.53 | 3.94 | 3.42 | AT3G16690 | 2.47 | 3.33 | 3.80 | 4.80 | 3.61 |
| AT1G62620 | 1.63 | 2.65 | 2.47 | 3.52 | 2.16 | AT3G17680 | 0.36 | 0.33 | 0.24 | 0.17 | 0.18 |
| AT1G65510 | 1.73 | 2.13 | 2.74 | 4.19 | 4.52 | AT3G23800 | 0.45 | 0.46 | 0.40 | 0.33 | 0.28 |
| AT1G65920 | 0.47 | 0.37 | 0.31 | 0.36 | 0.26 | AT3G24670 | 0.33 | 0.32 | 0.32 | 0.38 | 0.43 |
| AT1G68230 | 2.84 | 2.42 | 2.55 | 2.59 | 3.18 | AT3G28290 | 0.23 | 0.29 | 0.18 | 0.27 | 0.32 |
| AT1G71740 | 1.84 | 2.19 | 2.84 | 3.04 | 2.88 | AT3G47210 | 1.88 | 2.53 | 2.73 | 3.50 | 2.66 |
| AT3G47250 | 3.64 | 3.68 | 4.89 | 5.15 | 14.53 | AT5G06200 | 1.70 | 1.94 | 2.10 | 1.99 | 2.16 |
| AT3G51410 | 0.30 | 0.32 | 0.32 | 0.21 | 0.19 | AT5G08240 | 1.61 | 1.79 | 2.31 | 2.56 | 3.14 |
| AT3G51970 | 2.41 | 2.49 | 2.88 | 3.02 | 2.69 | AT5G11540 | 4.44 | 5.32 | 5.68 | 6.69 | 5.10 |
| AT3G53540 | 0.37 | 0.38 | 0.35 | 0.41 | 0.57 | AT5G15290 | 1.94 | 2.43 | 2.42 | 2.99 | 2.83 |
| AT3G56480 | 2.59 | 2.21 | 2.39 | 2.86 | 2.29 | AT5G18470 | 0.21 | 0.13 | 0.18 | 0.24 | 0.30 |
| AT3G59370 | 2.30 | 2.91 | 2.99 | 3.33 | 3.19 | AT5G18860 | 1.95 | 2.02 | 2.08 | 3.13 | 2.71 |
| AT3G59900 | 0.31 | 0.43 | 0.39 | 0.39 | 0.33 | AT5G18970 | 2.90 | 2.49 | 3.58 | 3.98 | 3.94 |
| AT3G60520 | 0.34 | 0.27 | 0.28 | 0.30 | 0.42 | AT5G19930 | 1.65 | 1.64 | 1.64 | 1.84 | 1.74 |
| AT4G01410 | 0.44 | 0.40 | 0.27 | 0.54 | 0.59 | AT5G22310 | 0.27 | 0.37 | 0.31 | 0.46 | 0.35 |
| AT4G08300 | 3.11 | 3.06 | 3.20 | 4.13 | 2.72 | AT5G23750 | 2.13 | 3.60 | 4.16 | 4.93 | 3.96 |
| AT4G10910 | 2.34 | 4.86 | 4.65 | 4.49 | 3.84 | AT5G24870 | 1.80 | 2.16 | 2.17 | 2.71 | 2.22 |
| AT4G12080 | 1.67 | 1.88 | 2.05 | 2.09 | 1.96 | AT5G34940 | 0.63 | 0.49 | 0.46 | 0.44 | 0.54 |
| AT4G13210 | 0.33 | 0.29 | 0.25 | 0.27 | 0.18 | AT5G37300 | 2.73 | 3.86 | 3.03 | 5.67 | 4.08 |
| AT4G15920 | 8.31 | 13.52 | 17.08 | 23.20 | 17.58 | AT5G38930 | 0.36 | 0.33 | 0.24 | 0.16 | 0.18 |
| AT4G25780 | 7.67 | 9.02 | 11.52 | 9.00 | 9.59 | AT5G44410 | 2.20 | 3.37 | 3.27 | 2.89 | 2.57 |
| AT4G28085 | 1.98 | 2.86 | 4.84 | 3.16 | 2.58 | AT5G44580 | 0.22 | 0.22 | 0.21 | 0.14 | 0.13 |
| AT4G31000 | 0.46 | 0.55 | 0.61 | 0.51 | 0.50 | AT5G47240 | 1.12 | 3.96 | 4.32 | 8.92 | 7.89 |
| AT4G32920 | 2.38 | 2.39 | 2.35 | 2.81 | 1.91 | AT5G47950 | 1.93 | 1.93 | 2.55 | 4.37 | 3.47 |
| AT4G34560 | 1.70 | 2.00 | 1.85 | 2.51 | 2.53 | AT5G48900 | 0.60 | 0.55 | 0.48 | 0.58 | 0.53 |
| AT4G35150 | 0.33 | 0.32 | 0.28 | 0.31 | 0.27 | AT5G49900 | 2.44 | 2.24 | 2.96 | 3.82 | 2.96 |
| AT4G36520 | 2.02 | 2.71 | 2.70 | 2.99 | 2.51 | AT5G53190 | 4.11 | 4.35 | 6.92 | 7.32 | 4.49 |
| AT4G39840 | 0.54 | 0.37 | 0.29 | 0.36 | 0.32 | AT5G53830 | 0.29 | 0.40 | 0.39 | 0.30 | 0.38 |
| AT5G01210 | 0.27 | 0.33 | 0.31 | 0.37 | 0.48 | AT5G58660 | 0.26 | 0.34 | 0.27 | 0.40 | 0.56 |
| AT5G01300 | 3.16 | 1.40 | 1.40 | 2.28 | 1.52 | AT5G66440 | 0.42 | 0.30 | 0.31 | 0.32 | 0.24 |
| AT5G04080 | 1.96 | 2.48 | 2.55 | 3.07 | 3.65 | AT5G66780 | 0.04 | 0.78 | 0.86 | 1.48 | 1.24 |
| AT5G05180 | 1.78 | 1.79 | 1.95 | 1.98 | 1.87 | | | | | | |

*Data are means of two microarray experiments and normalized to all sample medium.
I. Ratio of WT (no treatment) to etol-4 (no treatment).
II. Ratio of etol-4 (treated with 9393) to etol-4 (no treatment).
III. Ratio of etol-4 (treated with 9370) to etol-4 (no treatment).
IV. Ratio of etol-4 (treated with 7303) to etol-4 (no treatment).
V. Ratio of etol-4 (treated with AVG) to etol-4 (no treatment).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of improving the quality of harvested plants comprising providing to said plants an effective amount of a compound of formula I:

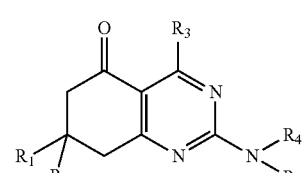

(I)

wherein $R_1$, $R_2$, and $R_3$ independently are H, optionally substituted $C_1$-$C_8$ alkyl, optionally substituted aryl, or optionally substituted heteroaryl; and R$_4$ and R$_5$ independently are H, optionally substituted C$_1$-C$_8$ alkyl, optionally substituted cycloalkyl, optionally substituted aryl, or optionally substituted heteroaryl.

2. The method of claim 1, wherein R$_1$ is H and R$_2$ is optionally substituted phenyl.

3. The method of claim 2, wherein the phenyl is substituted with alkoxy, halogen, or C$_1$-C$_8$ alkyl.

4. The method of claim 1, wherein R$_1$ and R$_2$ independently are optionally substituted C$_1$-C$_8$ alkyl or H.

5. The method of claim 4, wherein R$_1$ and R$_2$ independently are CH$_3$ or H.

6. The method of claim 5, wherein R$_1$ is CH$_3$ and R$_2$ is CH$_3$.

7. The method of claim 1, wherein R$_3$ is optionally substituted C$_1$-C$_8$ alkyl.

8. The method of claim 1, wherein R$_3$ is H, methyl, ethyl, or n-propyl.

9. The method of claim 1 where said compound is applied to the leaves, buds, fruits and/or flowers of the plants.

10. The method of claim 1, wherein said compound is applied to the roots of the plants.

11. The method of claim 1, wherein the improved quality of harvested plants is maintaining the freshness and quality of leaves, buds, fruits and/or flowers after harvest.

12. The method of claim 1, wherein the improved quality of harvested plants is prolonging the vase life of cut flowers.

13. The method of claim 1, wherein the compound is provided to said plants prior to harvesting the plants.

14. The method of claim 1, wherein the compound is provided to said plants after harvesting the plants.

* * * * *